(12) United States Patent
Berezhna et al.

(10) Patent No.: US 10,288,557 B2
(45) Date of Patent: May 14, 2019

(54) SPECTRAL DIFFERENTIATION OF HISTOLOGICAL STAINS

(71) Applicant: Abbott Laboratories, Abbott Park, IL (US)

(72) Inventors: Svitlana Y. Berezhna, Los Gatos, CA (US); Rene Nieves Alicea, San Francisco, CA (US); Ema C. Olah, Ventura, CA (US)

(73) Assignee: Abbott Laboratories, Abbott Park, IL (US)

(*) Notice: Subject to any disclaimer, the term of this patent is extended or adjusted under 35 U.S.C. 154(b) by 195 days.

(21) Appl. No.: 15/379,119

(22) Filed: Dec. 14, 2016

(65) Prior Publication Data

US 2017/0176325 A1  Jun. 22, 2017

Related U.S. Application Data

(60) Provisional application No. 62/269,204, filed on Dec. 18, 2015.

(51) Int. Cl.
*G01N 21/31* (2006.01)
*G01N 1/30* (2006.01)
(Continued)

(52) U.S. Cl.
CPC ............. *G01N 21/314* (2013.01); *G01J 1/00* (2013.01); *G01N 1/30* (2013.01); *G01N 21/31* (2013.01);
(Continued)

(58) Field of Classification Search
CPC ............ G01N 1/30; G01N 1/31; G01N 21/31; G01N 21/314; G01N 33/4833
See application file for complete search history.

(56) References Cited

U.S. PATENT DOCUMENTS 5,162,868 A   11/1992 Ando
6,160,617 A * 12/2000 Yang ..................... G01J 3/2823
                                                           356/300
(Continued)

FOREIGN PATENT DOCUMENTS

WO      2014089478      6/2014

OTHER PUBLICATIONS

Horobin & Walter. (1987) "Understanding Romanowsky staining"Histochemistry, 86:331-336.
(Continued)

*Primary Examiner* — Jennifer Wecker
(74) *Attorney, Agent, or Firm* — Edward J. Baba; Bozicevic, Field & Francis LLP

(57) ABSTRACT

The instant disclosure provides spectrophotometric methods for assessing histological stains used in a histology analyzer. The methods find use in various assessments including determinations of the identity of a histological stain, determinations of the quality of a histological stain, etc. Also included are devices and systems for practicing the described methods. The instant disclosure also provides computer readable media containing libraries of reference spectrophotometric characteristics of histological stains useful in assessing a histological stain used in a histology analyzer. Also provided is computer readable media containing instructions that cause a computing device to perform steps for making an assessment of a histological stain.

38 Claims, 9 Drawing Sheets

| Absorbance peak for Azures/Methylene Blue/Thionin (~655nm) 1:200 dilutions in DI water | | | | |
|---|---|---|---|---|
| WG | | MG | | |
| 50% of Low spec | 0.48 | 50% of Low spec | 0.30 | |
| 67% of Low spec | 0.63 | 67% of Low spec | 0.40 | |
| 83% of Low spec | 0.79 | 83% of Low spec | 0.50 | |
| LOW manufacturing spec / 100% of Low spec | 0.95 | 100% of Low spec | 0.60 | |
| Target / Target | 1.05 | Target | 0.70 | |
| HIGH manufacturing spec / 100% of High spec | 1.15 | 100% of High spec | 0.80 | |
| 110% of High spec | 1.27 | 110% of High spec | 0.88 | |

(51) Int. Cl.
*G01N 33/483* (2006.01)
*G01J 3/00* (2006.01)
*G01J 1/00* (2006.01)
*G01N 1/31* (2006.01)
*G01J 3/10* (2006.01)

(52) U.S. Cl.
CPC ............ *G01N 33/4833* (2013.01); *G01J 3/10* (2013.01); *G01N 2021/3196* (2013.01)

(56) References Cited

U.S. PATENT DOCUMENTS

| | | | |
|---|---|---|---|
| 6,165,734 A * | 12/2000 | Garini | C12Q 1/6841 435/14 |
| 6,643,016 B2 | 11/2003 | Garver et al. | |
| 7,262,844 B2 | 8/2007 | Larsen et al. | |
| 7,359,049 B2 | 4/2008 | Fujita | |
| 7,787,120 B2 | 8/2010 | Yamazaki et al. | |
| 7,932,095 B2 | 4/2011 | Herpst | |
| 8,049,884 B2 | 11/2011 | Tsukuda | |
| 8,115,922 B2 | 2/2012 | Webster et al. | |
| 8,189,199 B2 | 5/2012 | Robertson et al. | |
| 8,502,969 B2 | 8/2013 | Magnusson et al. | |
| 8,638,433 B1 | 1/2014 | Amend et al. | |
| 2006/0292599 A1 * | 12/2006 | Ritz | C12Q 1/6881 435/6.11 |
| 2008/0070324 A1 * | 3/2008 | Floyd | G01N 33/54393 436/518 |
| 2008/0241965 A1 * | 10/2008 | Schabacker | G01N 33/6827 436/536 |
| 2009/0048785 A1 * | 2/2009 | Katzir | C12Q 1/6841 702/20 |
| 2014/0038206 A1 * | 2/2014 | Holmes | G01N 21/17 435/7.21 |
| 2014/0267672 A1 * | 9/2014 | Morrison | G01N 21/6458 348/79 |

OTHER PUBLICATIONS

Marshall et al. (1978) "Staining properties and stability of a standardised Romanowsky stain" J Clin Pathol , 31(3):280-2.
Marshall et al. (1975) "A standardized Romanowsky stain prepared from purified dyes" J Clin Pathol. 28(11):920-3.
Marshall et al. (1975) "An evaluation of some commerical Romanowsky stains" J Clin Pathol 28(8):680-5.

\* cited by examiner

| Absorbance peak for Azures/Methylene Blue/Thionin (~655nm) 1:200 dilutions in DI water | | | |
|---|---|---|---|
| WG | | MG | |
| 50% of Low spec | 0.48 | 50% of Low spec | 0.30 |
| 67% of Low spec | 0.63 | 67% of Low spec | 0.40 |
| 83% of Low spec | 0.79 | 83% of Low spec | 0.50 |
| 100% of Low spec | 0.95 | 100% of Low spec | 0.60 |
| Target | 1.05 | Target | 0.70 |
| 100% of High spec | 1.15 | 100% of High spec | 0.80 |
| 110% of High spec | 1.27 | 110% of High spec | 0.88 |

LOW manufacturing spec / Target / HIGH manufacturing spec

SPECTRAL DIFFERENTIATION OF HISTOLOGICAL STAINS

CROSS-REFERENCE

This application claims the benefit of U.S. Provisional Patent Application No. 62/269,204 filed Dec. 18, 2015, which application is incorporated herein by reference in its entirety.

BACKGROUND

In histology many different stains and variations thereof are utilized. For example, in hematology, several different variations of a histologic Romanowsky staining are used for differentiation of blood cell types in a blood film smeared on a glass slide. In particular, two distinct types of stains known as Wright Giemsa (WG) and May Grunwald (MG) are used. Also, May Grunwald mixture is often used in combination with Giemsa stain producing May Grunwald Giemsa (MGG) formulation. All types of Romanowsky stain formulations are prepared from two main dyes, Eosin Y and Methylene Blue using a variety of processes, each one resulting in a distinct stain formulation Wright stain is a mixture of eosinates (Eosin Y dyes) of polychromed Methylene Blue. May Grunwald stain is a German equivalent of Jenner stain, which is a Methylene Blue eosinate similar to Wright stain but differing in not using polychromed Methylene Blue. Polychromed Methylene Blue is an alkaline solution of Methylene Blue that undergoes progressive oxidative demethylation with aging (ripening) to produce forms of all the tri, di, mono and non-methyl intermediates, resulting in a mixture of methylene blue, azures, thionine and methylene violet.

When applied to stain peripheral blood films, any type of Romanowsky stain will, in general, produce a similar type of cell coloration. However, small but important differences in stain formulation will allow for differentiating of specific conditions in the blood cells such as, for example, toxic granulation in neutrophils. If the stain formulation is not optimal (e.g., lacks sufficient fraction of pure Methylene Blue in proportion to its derivatives), the normal neutrophilic granules tend to overstain and look like toxic granules. The optimal stain composition also enhances the staining of nucleoli and polychromatophilic RBCs (reticulocytes). Therefore, it is important to maintain and tightly control the specific composition of any given stain formulation as achieved in optimization processes.

Because compositions of Romanowsky type stains are very similar, it is difficult, if not impossible, to discriminate between any (WG, MG or MGG) closely related stains and/or variations of the same stain by visual inspection or through the use of common laboratory instrumentation, such as measurement of stain pH.

In automated histology e.g., as performed by automated histological or hematological slide preparation devices, various stains may be used depending on the particular assay to be performed or user preferences. Automated slide preparation devices, regardless of whether a particular device uses a single stain or multiple stains, requires a human user to load the stain(s). As such, the stains may be inadvertently misidentified and the wrong stain may be loaded into the device. In addition, stains may arrive misidentified, unbeknownst to the device user, due, e.g., to accidental mislabeling or improper preparation. Shelf storage under inadequate conditions may affect stain composition, not noticeable by visual inspection.

Stain protocols are highly dependent on use of the proper stain. Thus, when a misidentified or incorrectly prepared stain is used, the procedure will likely produce an undesired result, e.g., sub-optimal coloration. While stain identity may be conclusively determined by complex analytical methods used to determine stain composition, e.g., high performance liquid chromatography (HPLC), these methods are arduous, consuming significant time and resources. HPLC also requires a set of reference analytes to identify peaks (bands) on a chromatogram which might be difficult to obtain for such a complex mixture as a polychomed Methylene Blue.

Methylene blue is a cationic dye (i.e., it produces positively charged ions or cations) which, in its pure form, exhibits two major absorption bands at 293 nm ($\pi$-$\pi$* transition) and 664 nm (n-$\pi$* transition) in aqueous solutions, with a 664 nm (producing blue color) band having a shoulder at 610 nm corresponding to the 0-1 vibronic transition. The specifics of absorption depend on a number of factors, including protonation, adsorption to other materials, and metachromasy—the formation of dimers and higher-order aggregates depending on concentration and other interactions. In turn, Eosin Y is an acidic dye (ionizes in solution to produce negatively charged ions or anions) which exhibits a major absorption band at 524 nm (producing red color).

Therefore, optical absorbance of a dye molecule is sensitive to modifications which the dye molecule may undergo in the process of stain preparation.

SUMMARY

Aspects of the instant disclosure include a method of assessing a histological stain used in a histology analyzer, the method comprising: measuring on a spectrophotometer the absorbance spectrum of the histological stain over a predefined range; identifying one or more wavelengths of peak absorbance from the measured spectrum; comparing the one or more identified wavelengths of peak absorbance to a library comprising reference wavelengths of peak absorbance for a plurality of histological stains; and assessing the histological stain based on the comparison.

Other aspects include assessing a histological stain used in a histology analyzer to determine the identity of a histological stain, to determine the quality of the histological stain. In some aspects the method includes generating a report of the assessment, wherein the report comprises stain-specific information including e.g., the identity of the histological stain, the quality of the histological stain, one or more wavelengths of peak absorbance, one or more absorbance measurements over the predefined range or a portion thereof, or combinations thereof.

In certain aspects of the instant disclosure the predefined range over which the absorbance spectrum is measured is or is within 200 nm to 800 nm, 500 nm to 700, 600 nm to 700 nm, 640 nm to 670 nm, 500 nm to 550 nm, or 200 nm to 400 nm.

In some aspects the method includes measuring on a spectrophotometer the absorbance spectrum of the histological stain over two or more predefined ranges, including e.g., wherein the two or more predefined ranges comprise a first predefined range that is or is within 500 nm to 700 nm and a second predefined range that is or is within 200 nm to 400 nm.

Other aspects include, diluting the histological stain prior to measuring the absorbance spectrum with a solvent where the specific dilution and the specific solvent used in diluting the stain specifically correspond to the reference wavelengths of peak absorbance to which the measured wavelengths are compared, e.g., where the reference wavelengths of peak absorbance were obtained from reference samples diluted to the same dilution and with the same solvent as the histological stain being measured. In some aspects, the stain is diluted to 1:200 with water.

In other aspects, the method of assessing a histological stain may include preparing a plurality of dilutions of the histological stain and performing the method steps for each dilution of the plurality of dilutions of the histological stain. In other aspects, the method of assessing a histological stain may include preparing a first dilution and a second dilution, wherein the second dilution is half the concentration of the first dilution.

In other aspects, the method of assessing a histological stain may include identifying a spectral shift value from a measured spectrum. In some aspects, the library of reference wavelengths of peak absorbance further includes a plurality of spectral shift values for a plurality of histological stains and the comparing further comprises comparing the measured spectral shift value to the library.

In other aspects, the method of assessing a histological stain may include identifying a peak-width-at-half-maximum-absorbance value from the measured spectrum. In some aspects, the library of reference wavelengths of peak absorbance further comprises a plurality of peak-width-at-half-maximum-absorbance values for a plurality of histological stains and the comparing further comprises comparing the peak-width-at-half-maximum-absorbance value to the library.

Aspects of the instant disclosure include assessing a plurality of histological stains including where the plurality of histological stains includes Romanowsky stains, including e.g., Wright Giemsa, May Grunwald and May Grunwals Giemsa.

In other aspects, the method of assessing a histological stain may include measuring on a spectrophotometer the absorbance spectrum of the histological stain where the absorbance spectrum is measured with a resolution of at least 1 nm.

In other aspects, the library of reference wavelengths of peak absorbance may include a reference wavelength peak of absorbance at essentially 656 nm for May Grunwald, a plurality of spectral shift values for a plurality of May Grunwald stain compositions wherein the spectral shift value is measured from the reference wavelength peak of absorbance of 656 nm for May Grunwald and/or a plurality of peak-width-at-half-maximum-absorbance values for a plurality of May Grunwald stain compositions.

In other aspects, the library of reference wavelengths of peak absorbance may include a reference wavelength peak of absorbance at essentially 659 nm for Wright Giemsa, a plurality of spectral shift values for a plurality of Wright Giemsa stain compositions wherein the spectral shift value is measured from the reference wavelength peak of absorbance of 659 nm for Wright Giemsa and/or a plurality of peak-width-at-half-maximum-absorbance values for a plurality of Wright Giemsa stain compositions.

In other aspects, the library of reference wavelengths of peak absorbance may include a reference wavelength peak of absorbance for May Grunwald Giemsa, a plurality of spectral shift values for a plurality of May Grunwald Giemsa stain compositions wherein the spectral shift value is measured from a reference wavelength peak of absorbance for May Grunwald Giemsa and/or a plurality of peak-width-at-half-maximum-absorbance values for a plurality of May Grunwald Giemsa stain compositions.

In other aspects the method includes making a plurality of assessments of the histological stain over time in order to monitor stain quality.

In other aspects the method includes transferring an aliquot of the histological stain from a storage container into an analysis vessel prior to the measuring, e.g., where the analysis vessel is a cuvette, a capillary or a multi-well plate.

Aspects of the instant disclosure include wherein the measuring of the method takes place within a histology analyzer or wherein the measuring takes place outside of a histology analyzer. In some aspects, after the measuring is performed outside a histology analyzer the absorbance spectrum of the histological stain, one or more wavelengths of peak absorbance derived therefrom or a combination thereof is transferred to the histology analyzer. In certain aspects, the absorbance spectrum of the histological stain, one or more wavelengths of peak absorbance derived therefrom or a combination thereof is transferred through a wired data connection connecting the spectrophotometer to the histology analyzer. In certain aspects, the absorbance spectrum of the histological stain, one or more wavelengths of peak absorbance derived therefrom or a combination thereof is transferred using a computer-readable storage medium.

Aspects of the instant disclosure also include a device for assessing a histological stain used in a histology analyzer, the device comprising: a spectrophotometer configured to measure the absorbance spectrum of the histological stain over a predefined range; a library of reference wavelengths of peak absorbance for a plurality of histological stains; spectra processing circuitry configured to: i) identify one or more wavelengths of peak absorbance from the measured spectrum; ii) compare the one or more wavelengths of peak absorbance to the library to make an assessment of the histological stain; and a signal system configured to report the result of the assessment.

In other aspects, the report of the device includes stain-specific information including, e.g., the identity of the histological stain, the quality of the histological stain, one or more wavelengths of peak absorbance, one or more absorbance measurements over the predefined range or a portion thereof, or combinations thereof. In some aspects, the report includes a determination of the identity of the histological stain and/or a determination of the quality of the histological stain.

In other aspects, the device includes a user interface configured for a user to input an assumed identity of the histological stain and spectra processing circuitry configured to compare the assumed identity of the histological stain to the assessed identity of the histological stain and output a result as to whether the assumed identity and the assessed identity of the histological stain match.

In other aspects, the device includes a signal system configured to alert the user when the assumed identity and the assessed identity of the histological stain do not match, configured to alert the user when the quality of the histological stain is below a predetermined threshold and/or configured to alert the user when the quality of the histological stain is below a user specified threshold.

In other aspects the range over which the absorbance spectrum of the histological stain is measured by the device includes e.g., where the predefined range is or is within 200 nm to 800 nm, 500 nm to 700 nm, 600 nm to 700 nm, 640 nm to 670 nm, 500 nm to 550 nm or 200 nm to 400 nm. In some aspects, the predefined range includes two or more predefined sub-ranges including e.g., a first predefined sub-range that is or is within 500 nm to 700 nm and a second predefined sub-range that is or is within 200 nm to 400 nm.

In other aspects, the device includes a sample preparation module configured to extract a sample of the histological stain, including e.g., where the module is configured to dispense the sample into an analysis vessel that is compatible with a spectrophotometer. In some aspects, the analysis vessel is a cuvette, a capillary or a multi-well plate. In some aspects, the sample preparation module is configured to prepare one or more dilutions from a sample of the histological stain.

In other aspects, the device includes a spectrophotometer configured to measure the absorbance spectrum with a resolution of at least 1 nm or at least 0.5 nm.

In other aspects, the library of the device includes a reference wavelength peak of absorbance at essentially 656 nm for May Grunwald, a reference wavelength peak of absorbance at essentially 659 nm for Wright Giemsa.

In other aspects, the device includes spectra processing circuitry that is configured to trigger the device to measure the absorbance spectrum of the histological stain according to a predetermined time schedule, including e.g., at least monthly, at least bimonthly, at least weekly, at least biweekly, at least every two days, at least daily.

In other aspects, the device includes a container for storage of the histological stain or an aliquot thereof.

In other aspects, the device is housed within the histology analyzer.

Aspects of the instant disclosure include a system for assessing a histological stain used in a histology analyzer, the system comprising: an absorbance analyzer comprising: i) a spectrophotometer configured to measure the absorbance spectrum of the histological stain over a predefined range; ii) a library of reference wavelengths of peak absorbance for a plurality of histological stains; iii) spectra processing circuitry configured to: 1) identify one or more wavelengths of peak absorbance from the measured spectrum; and 2) compare the one or more wavelengths of peak absorbance to the library to make an assessment of the histological stain; and iv) a removable computer-readable storage medium configured to store the result of the assessment; and a histology analyzer comprising: i) a port configured to receive the removable computer-readable storage medium; and ii) a signal system configured to report the result of the assessment.

In other aspects, the report of the system includes stain-specific information including the identity of the histological stain, the quality of the histological stain, one or more wavelengths of peak absorbance, one or more absorbance measurements over the predefined range or a portion thereof, or combinations thereof. In some aspects, the report includes a determination of the identity of the histological stain or a determination of the quality of the histological stain.

In other aspects, the system includes an absorbance analyzer or histology analyzer or both analyzers that include a user interface configured for a user to input an assumed identity of the histological stain. In some aspects, the spectra processing circuitry of the system is further configured to compare the assumed identity of the histological stain to the assessed identity of the histological stain and output a result as to whether the assumed identity and the assessed identity of the histological stain match. In some aspects, the signal system is configured to alert the user when the assumed identity and the assessed identity of the histological stain do not match, when the quality of the histological stain is below a predetermined threshold or when the quality of the histological stain is below a user specified threshold.

In other aspects, the predefined range of the system over which the absorbance spectrum of the histological stain measured is or is within 200 nm to 800 nm, 500 nm to 700 nm, 600 nm to 700 nm, 640 nm to 670 nm, 500 nm to 550 nm or 200 nm to 400 nm. In some aspects, the predefined range comprises two or more predefined sub-ranges, including e.g., a first predefined sub-range that is or is within 500 nm to 700 nm and a second predefined sub-range that is or is within 200 nm to 400 nm.

In other aspects, the spectrophotometer of the system is configured to measure the absorbance spectrum with a resolution of at least 1 nm or at least 0.5 nm.

In other aspects, the library of the system includes a reference wavelength peak of absorbance at essentially 656 nm for May Grunwald or a reference wavelength peak of absorbance at essentially 659 nm for Wright Giemsa.

Aspects of the instant disclosure include a system for assessing a histological stain used in a histology analyzer, the system comprising: an absorbance analyzer comprising: i) a spectrophotometer configured to measure the absorbance spectrum of the histological stain over a predefined range; and ii) a removable computer-readable storage medium configured to store the measured spectrum; and a histology analyzer comprising: i) a library of reference wavelengths of peak absorbance for a plurality of histological stains; ii) a port configured to receive the removable computer-readable storage medium and upload the measured spectrum; iii) spectra processing circuitry configured to: 1) identify one or more wavelengths of peak absorbance from the measured spectrum; and 2) compare the one or more wavelengths of peak absorbance to the library to make an assessment of the histological stain; and iv) a signal system configured to report the result of the assessment.

In other aspects, the report of the system includes stain-specific information including the identity of the histological stain, the quality of the histological stain, one or more wavelengths of peak absorbance, one or more absorbance measurements over the predefined range or a portion thereof, or combinations thereof. In some aspects, the report comprises a determination of the identity of the histological stain or a determination of the quality of the histological stain.

In other aspects, an absorbance analyzer or a histology analyzer or both analyzers of the system include a user interface configured for a user to input an assumed identity of the histological stain. In some aspects, the spectra processing circuitry is configured to compare the assumed identity of the histological stain to the assessed identity of the histological stain and output a result as to whether the assumed identity and the assessed identity of the histological stain match.

In other aspects, the system includes a signal system configured to alert the user when the assumed identity and the assessed identity of the histological stain do not match, when the quality of the histological stain is below a predetermined threshold, or when the quality of the histological stain is below a user specified threshold.

In other aspects, the predefined range of the system over which the absorbance spectrum is measured is or is within 200 nm to 800 nm, 500 nm to 700 nm, 600 nm to 700 nm, 640 nm to 670 nm, 500 nm to 550 nm or 200 nm to 400 nm. In some aspects, the predefined range comprises two or more predefined sub-ranges, including e.g., a first predefined sub-range that is or is within 500 nm to 700 nm and a second predefined sub-range that is or is within 200 nm to 400 nm.

In other aspects, the spectrophotometer of the system is configured to measure the absorbance spectrum with a resolution of at least 1 nm or at least 0.5 nm.

In other aspects, the library of the system included a reference wavelength peak of absorbance at essentially 656 nm for May Grunwald, a reference wavelength peak of absorbance at essentially 659 nm for Wright Giemsa.

Aspects of the instant disclosure include a non-transitory computer readable medium storing a library of reference wavelengths of peak absorbance for a plurality of histological stains. In some aspects, the library includes a plurality of spectral shift values for a plurality of histological stains and/or a plurality of peak-width-at-half-maximum-absorbance values for a plurality of histological stains. In some aspects, the histological stains of the library include Romanowsky stains, including e.g., Wright Giemsa, May Grunwald and/or May Grunwals Giemsa.

Aspects of the instant disclosure include a non-transitory computer readable medium storing instructions that, when executed by a computing device, cause the computing device to perform the steps of: a) comparing one or more input wavelengths of peak absorbance to a library of reference wavelengths of peak absorbance for a plurality of histological stains; and b) determining based on the comparison which histological stain of the plurality of histological stains matches the one or more input wavelengths of peak absorbance. In some aspects, the non-transitory computer readable medium also includes the library.

In other aspects, the library of the non-transitory computer readable medium includes a plurality of reference spectral shift values for a plurality of histological stains and the comparing caused by the instructions includes comparing one or more input spectral shift values to the library.

In other aspects, the library of the non-transitory computer readable medium includes a plurality of reference peak-width-at-half-maximum-absorbance values for a plurality of histological stains and the comparing caused by the instructions includes comparing one or more input peak-width-at-half-maximum-absorbance values to the library.

In other aspects, the histological stains of the library of the non-transitory computer readable medium includes a plurality of Romanowsky stains, including e.g., Wright Giemsa, May Grunwald and/or May Grunwals Giemsa.

BRIEF DESCRIPTION OF THE FIGURES

FIG. 1 provides the absorbance peaks at ~655 nm for various dilutions of within specification and not within specification formulations of Wright Giemsa (WG) and May Grunwald (MG) stains as described herein.

FIG. 2 provides for comparison example images of cells stained with within specification and not within specification formulations of WG.

DEFINITIONS

Figure 3:
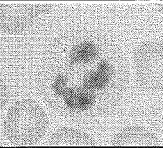
FIG. 3 provides for comparison example images of cells stained with within specification and not within specification formulations of MG.

The terms "spectrophotometry" and "spectrophotometric" as used herein generally refer to methods involving the use of a spectrophotometer. By "spectrophotometer" is generally meant a an instrument which measures the amount of light of one or more specified spectral wavelengths using a photometer, wherein the one or more wavelengths may be a discrete wavelength or color (e.g., a wavelength of a single size measured in nanometers (nm)) or a range of wavelengths or colors including, e.g., a plurality discrete wavelengths measured across a defined range of the spectrum. The amount of light measured on a spectrophotometer is generally related to the light that passes through a medium where the medium may be a substance of interest for which a spectrophotometric is being determined. The quantitative measurement of the light that passes through a medium is generally expressed in terms of or is referred to as absorbance. However, in some instances, a spectrophotometric measurement may also be referred to as or expressed in terms of reflection, transmittance, etc. The quantitative measurement obtained from a spectrophotometer may be a raw or total or absolute measurement (e.g., absolute absorbance) or the measurement may be a relative measurement, e.g., a percentage or ratio, including, e.g., a percentage of a reference value or control measurement (e.g., percent absorbance, percent transmittance, etc.).

The terms "spectra" and "spectrum" as used herein generally refer to a collection or band of wavelengths or colors of electromagnetic radiation within the visible and adjacent ranges including but not limited to, e.g., ultraviolet-visible (UV-vis) range, visible range (ultraviolet range, near ultraviolet range, violet range, blue range, green range, yellow range, orange range, red range, infrared range, near infrared range, mid infrared range, far infrared range, etc. In some instances, a spectrum may refer to the total range of wavelengths across which light was measured. In some instances, a spectrum may refer to a portion of the range of wavelengths across which light was measured. For example, a spectrum obtain from a spectrophotometer may reflect the entire measured range of wavelengths or a portion of the measured wavelengths.

The term "assessing" includes any form of measurement, and includes determining if an element is present or not. The terms "determining", "measuring", "evaluating", "assessing" and "assaying" are used interchangeably and include quantitative and qualitative determinations. Assessing may be relative or absolute. "Assessing the identity of" includes determining the most likely identity of a particular compound or formulation or substance, and/or determining whether a predicted compound or formulation or substance is present or absent. "Assessing the quality of" includes making a qualitative or quantitative assessment of quality e.g., through the comparisons of a determined value to a reference or standard of known quality.

The term "histology" and "histological" as used herein generally refers to microscopic analysis of the cellular anatomy and/or morphology of cells obtained from a multicellular organism including but not limited to plants and animals. As such, a "histological stain" refers to a stain used in the analysis of cellular anatomy and/or morphology and a "histology analyzer" refers to an instrument that analyzes the anatomy and/or morphology of cells obtained from a multicellular animal. As used herein a histology analyzer will generally refer to an instrument that uses one or more histological stains to make a histological assessment.

The term "cytology" and "cytological" as used herein generally refers to a subclass of histology that includes the microscopic analysis of individual cells, dissociated cells, loose cells, clusters of cells, etc. Cells of a cytological sample may be cells in or obtained from one or more bodily fluids. As such, a "cytological stain" refers to a stain used in the analysis of individual cells, dissociated cells, loose cells, clusters of cells, etc. and a "cytology analyzer" refers to an instrument that analyzes the anatomy and/or morphology of individual cells, dissociated cells, loose cells, clusters of cells, etc. As used herein a cytology analyzer will generally refer to an instrument that uses one or more cytological stains to make a cytological assessment.

The term "bodily fluid" as used herein generally refers to fluids derived from a "biological sample" which encompasses a variety of sample types obtained from an individual or a population of individuals and can be used in a diagnostic, monitoring or screening assay. The definition encompasses blood and other liquid samples of biological origin. The definition also includes samples that have been manipulated in any way after their procurement, such as by mixing or pooling of individual samples, treatment with reagents, solubilization, or enrichment for certain components, such as nucleated cells, non-nucleated cells, pathogens, etc.

The term "biological sample" encompasses a clinical sample, and also includes cells in culture, cell supernatants, cell lysates, serum, plasma, biological fluid, and tissue samples. The term "biological sample" includes urine, saliva, cerebrospinal fluid, interstitial fluid, ocular fluid, synovial fluid, blood fractions such as plasma and serum, and the like.

The term "inputting", as used herein, is used to refer to any way of entering information into a computer, such as, e.g., through the use of a user interface. For example, in certain cases, inputting can involve selecting a reference spectrum or a spectral characteristic or library thereof that is already present on a computer system. In other cases, inputting can involve adding a spectrum or a spectral characteristic to a computer system, e.g., by measuring the spectrum of a sample on a device capable of interfacing with a computer. Inputting can also be done using a user interface.

As used herein, the term "executing" is used to refer to an action that a user takes to initiate a program.

The terms "control", "control assay", "control sample" and the like, refer to a sample, test, or other portion of an experimental or diagnostic procedure or experimental design for which an expected result is known with high certainty, e.g., in order to indicate whether the results obtained from associated experimental samples are reliable, indicate to what degree of confidence associated experimental results indicate a true result, and/or to allow for the calibration of experimental results. For example, in some instances, a control may be a "negative control" assay such that an essential component of the assay is excluded such that an experimenter may have high certainty that the negative control assay will not produce a positive result. In some instances, a control may be "positive control" such that all components of a particular assay are characterized and known, when combined, to produce a particular result in the assay being performed such that an experimenter may have high certainty that the positive control assay will not produce a positive result. Controls may also include "blank" samples, "standard" samples (e.g., "gold standard" samples), validated samples, etc.

DETAILED DESCRIPTION

The instant disclosure provides spectrophotometric methods for assessing histological stains used in a histology analyzer. The methods find use in various assessments including determinations of the identity of a histological stain, determinations of the quality of a histological stain, etc. Also included are devices and systems for practicing the described methods. The instant disclosure also provides computer readable media containing libraries of reference spectrophotometric characteristics of histological stains useful in assessing a histological stain used in a histology analyzer. Also provided is computer readable media containing instructions that cause a computing device to perform steps for making an assessment of a histological stain.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating un-recited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Methods

The instant disclosure includes spectrophotometric methods for assessing histological stains used in a histology analyzer. Aspects of the instant disclosure include measuring spectrophotometric characteristics of a subject histological stain using a spectrophotometer to identify one or more characteristics that are specific to a particular stain and/or stain formulation for various purposes.

Spectrophotometric Characteristics

Spectrophotometric characteristics of interest include but are not limited to the position of one or more peaks, the width of one or more peaks and the peak absorbance of one or more peaks. In some instances, Spectrophotometric characteristics of interest include but are not limited to relative peak characteristics between two or more different peaks including but not limited to the relative positions between two or more peaks of the spectrum, the relative peak absorbances of two or more peaks of the spectrum, the relative widths of two or more peaks of the spectrum, etc.

Without being bound by theory, aspects of the instant disclosure are based on the discovery that the spectral characteristics of a particular stain formulation are dependent on the interaction of the individual components of the stain and are dependent on the relative amounts of the individual stain components. For example, the relative amounts of components X and Y of a stain may result in different spectral characteristics in formulation 1 as compared to formulation 2 where formulations 1 and 2 differ in the relative amounts of component X to component Y, and their mode of preparation. Thus, even those stains having only slightly different ratios of stain components will vary in their spectral characteristics. Accordingly, each histological stain formulation has specific spectral characteristics that may be measured and used for various assessments.

In some instances, a specific spectral characteristic of a particular histological stain or stain formulation may be a position of an absorbance peak obtained by measuring an absorbance spectrum of the histological stain on a spectrophotometer. The position of an absorbance peak may be determined through various methods. For example, in a number of embodiments described herein the position of an absorbance peak is determined based on the peak absorbance of the peak where the term "peak absorbance" (also referred to as wavelength of maximum absorbance (i.e., λmax)), as used herein, refers to the wavelength at which the peak reaches its highest absorbance maximum. In other instances, the position of the peak may be determined by means other than the peak absorbance including but not limited to e.g., the wavelength corresponding to the mean of the width of the peak, the wavelength corresponding to the mean of the width of the peak at half the maximum absorbance, the wavelength corresponding to the median of the width of the peak, the wavelength corresponding to the median of the width of the peak at half the maximum absorbance, etc.

In some instances, the position of the peak may be determined with consideration of any minor peaks or "shoulders" present within the spectral band of the major peak. In some instances, the position of the peak may be determined without consideration of any minor peaks or "shoulders" present within the spectral band of the major peak.

The position of the peak may be expressed in absolute terms including e.g., according to the wavelength of the peak. The absolute position of an absorbance peak will vary depending on the particular stain formulation and may range from about 200 nm or less to about 800 nm or more including but not limited to e.g., 200 nm to 800 nm, 200 nm to 700 nm, 200 nm to 600 nm, 200 nm to 500 nm, 200 nm to 400 nm, 300 nm to 800 nm, 300 nm to 700 nm, 300 nm to 600 nm, 300 nm to 500 nm, 300 nm to 400 nm, 400 nm to 800 nm, 400 nm to 700 nm, 400 nm to 600 nm, 400 nm to 500 nm, 500 nm to 800 nm, 500 nm to 700 nm, 500 nm to 600 nm, 500 nm to 550 nm, 600 nm to 800 nm, 600 nm to 700 nm, 600 nm to 670 nm, 640 nm to 700 nm, 640 nm to 670 nm, etc.

In some instances, the absolute position of an absorbance peak may be 200 nm, 201 nm, 202 nm, 203 nm, 204 nm, 205 nm, 206 nm, 207 nm, 208 nm, 209 nm, 210 nm, 211 nm, 212 nm, 213 nm, 214 nm, 215 nm, 216 nm, 217 nm, 218 nm, 219 nm, 220 nm, 221 nm, 222 nm, 223 nm, 224 nm, 225 nm, 226 nm, 227 nm, 228 nm, 229 nm, 230 nm, 231 nm, 232 nm, 233 nm, 234 nm, 235 nm, 236 nm, 237 nm, 238 nm, 239 nm, 240 nm, 241 nm, 242 nm, 243 nm, 244 nm, 245 nm, 246 nm, 247 nm, 248 nm, 249 nm, 250 nm, 251 nm, 252 nm, 253 nm, 254 nm, 255 nm, 256 nm, 257 nm, 258 nm, 259 nm, 260 nm, 261 nm, 262 nm, 263 nm, 264 nm, 265 nm, 266 nm, 267 nm, 268 nm, 269 nm, 270 nm, 271 nm, 272 nm, 273 nm, 274 nm, 275 nm, 276 nm, 277 nm, 278 nm, 279 nm, 280 nm, 281 nm, 282 nm, 283 nm, 284 nm, 285 nm, 286 nm, 287 nm, 288 nm, 289 nm, 290 nm, 291 nm, 292 nm, 293 nm, 294 nm, 295 nm, 296 nm, 297 nm, 298 nm, 299 nm, 300 nm, 301 nm, 302 nm, 303 nm, 304 nm, 305 nm, 306 nm, 307 nm, 308 nm, 309 nm, 310 nm, 311 nm, 312 nm, 313 nm, 314 nm, 315 nm, 316 nm, 317 nm, 318 nm, 319 nm, 320 nm, 321 nm, 322 nm, 323 nm, 324 nm, 325 nm, 326 nm, 327 nm, 328 nm, 329 nm, 330 nm, 331 nm, 332 nm, 333 nm, 334 nm, 335 nm, 336 nm, 337 nm, 338 nm, 339 nm, 340 nm, 341 nm, 342 nm, 343 nm, 344 nm, 345 nm, 346 nm, 347 nm, 348 nm, 349 nm, 350 nm, 351 nm, 352 nm, 353 nm, 354 nm, 355 nm, 356 nm, 357 nm, 358 nm, 359 nm, 360 nm, 361 nm, 362 nm, 363 nm, 364 nm, 365 nm, 366 nm, 367 nm, 368 nm, 369 nm, 370 nm, 371 nm, 372 nm, 373 nm, 374 nm, 375 nm, 376 nm, 377 nm, 378 nm, 379 nm, 380 nm, 381 nm, 382 nm, 383 nm, 384 nm, 385 nm, 386 nm, 387 nm, 388 nm, 389 nm, 390 nm, 391 nm, 392 nm, 393 nm, 394 nm, 395 nm, 396 nm, 397 nm, 398 nm, 399 nm, 400 nm, 401 nm, 402 nm, 403 nm, 404 nm, 405 nm, 406 nm, 407 nm, 408 nm, 409 nm, 410 nm, 411 nm, 412 nm, 413 nm, 414 nm, 415 nm, 416 nm, 417 nm, 418 nm, 419 nm, 420 nm, 421 nm, 422 nm, 423 nm, 424 nm, 425 nm, 426 nm, 427 nm, 428 nm, 429 nm, 430 nm, 431 nm, 432 nm, 433 nm, 434 nm, 435 nm, 436 nm, 437 nm, 438 nm, 439 nm, 440 nm, 441 nm, 442 nm, 443 nm, 444 nm, 445 nm, 446 nm, 447 nm, 448 nm, 449 nm, 450 nm, 451 nm, 452 nm, 453 nm, 454 nm, 455 nm, 456 nm, 457 nm, 458 nm, 459 nm, 460 nm, 461 nm, 462 nm, 463 nm, 464 nm, 465 nm, 466 nm, 467 nm, 468 nm, 469 nm, 470 nm, 471 nm, 472 nm, 473 nm, 474 nm, 475 nm, 476 nm, 477 nm, 478 nm, 479 nm, 480 nm, 481 nm, 482 nm, 483 nm, 484 nm, 485 nm, 486 nm, 487 nm, 488 nm, 489 nm, 490 nm, 491 nm, 492 nm, 493 nm, 494 nm, 495 nm, 496 nm, 497 nm, 498 nm, 499 nm, 500 nm, 501 nm, 502 nm, 503 nm, 504 nm, 505 nm, 506 nm, 507 nm, 508 nm, 509 nm, 510 nm, 511 nm, 512 nm, 513 nm, 514 nm, 515 nm, 516 nm, 517 nm, 518 nm, 519 nm, 520 nm, 521 nm, 522 nm, 523 nm, 524 nm, 525 nm, 526 nm, 527 nm, 528 nm, 529 nm, 530 nm, 531 nm, 532 nm, 533 nm, 534 nm, 535 nm, 536 nm, 537 nm, 538 nm, 539 nm, 540 nm, 541 nm, 542 nm, 543 nm, 544 nm, 545 nm, 546 nm, 547 nm, 548 nm, 549 nm, 550 nm, 551 nm, 552 nm, 553 nm, 554 nm, 555 nm, 556 nm, 557 nm, 558 nm, 559 nm, 560 nm, 561 nm, 562 nm, 563 nm, 564 nm, 565 nm, 566 nm, 567 nm, 568 nm, 569 nm, 570 nm, 571 nm, 572 nm, 573 nm, 574 nm, 575 nm, 576 nm, 577 nm, 578 nm, 579 nm, 580 nm, 581 nm, 582 nm, 583 nm, 584 nm, 585 nm, 586 nm, 587 nm, 588 nm, 589 nm, 590 nm, 591 nm, 592 nm, 593 nm, 594 nm, 595 nm, 596 nm, 597 nm, 598 nm, 599 nm, 600 nm, 601 nm, 602 nm, 603 nm, 604 nm, 605 nm, 606 nm, 607 nm, 608 nm, 609 nm, 610 nm, 611 nm, 612 nm, 613 nm, 614 nm, 615 nm, 616 nm, 617 nm, 618 nm, 619 nm, 620 nm, 621 nm, 622 nm, 623 nm, 624 nm, 625 nm, 626 nm, 627 nm, 628 nm, 629 nm, 630 nm, 631 nm, 632 nm, 633 nm, 634 nm, 635 nm, 636 nm, 637 nm, 638 nm, 639 nm, 640 nm, 641 nm, 642 nm, 643 nm, 644 nm, 645 nm, 646 nm, 647 nm, 648 nm, 649 nm, 650 nm, 651 nm, 652 nm, 653 nm, 654 nm, 655 nm, 656 nm, 657 nm, 658 nm, 659 nm, 660 nm, 661 nm, 662 nm, 663 nm, 664 nm, 665 nm, 666 nm, 667 nm, 668 nm, 669 nm, 670 nm, 671 nm, 672 nm, 673 nm, 674 nm, 675 nm, 676 nm, 677 nm, 678 nm, 679 nm, 680 nm, 681 nm, 682 nm, 683 nm, 684 nm, 685 nm, 686 nm, 687 nm, 688 nm, 689 nm, 690 nm, 691 nm, 692 nm, 693 nm, 694 nm, 695 nm, 696 nm, 697 nm, 698 nm, 699 nm, 700 nm, 701 nm, 702 nm, 703 nm, 704 nm, 705 nm, 706 nm, 707 nm, 708 nm, 709 nm, 710 nm, 711 nm, 712 nm, 713 nm, 714 nm, 715 nm, 716 nm, 717 nm, 718 nm, 719 nm, 720 nm, 721 nm, 722 nm, 723 nm, 724 nm, 725 nm, 726 nm, 727 nm, 728 nm, 729 nm, 730 nm, 731 nm, 732 nm, 733 nm, 734 nm, 735 nm, 736 nm, 737 nm, 738 nm, 739 nm, 740 nm, 741 nm, 742 nm, 743 nm, 744 nm, 745 nm, 746 nm, 747 nm, 748 nm, 749 nm, 750 nm, 751 nm, 752 nm, 753 nm, 754 nm, 755 nm, 756 nm, 757 nm, 758 nm, 759 nm, 760 nm, 761 nm, 762 nm, 763 nm, 764 nm, 765 nm, 766 nm, 767 nm, 768 nm, 769 nm, 770 nm, 771 nm, 772 nm, 773 nm, 774 nm, 775 nm, 776 nm, 777 nm, 778 nm, 779 nm, 780 nm, 781 nm, 782 nm, 783 nm, 784 nm, 785 nm, 786 nm, 787 nm, 788 nm, 789 nm, 790 nm, 791 nm, 792 nm, 793 nm, 794 nm, 795 nm, 796 nm, 797 nm, 798 nm, 799 nm or 800 nm.

In some instances, the position of the peak may be expressed in relative terms including e.g., the position of the peak relative to a reference peak e.g., in a different stain, stain formulation or stain component. For example, the position of the peak may be expressed relative to a standard stain formulation including but not limited to e.g., a validated formulation of the stain, a target formulation of the stain, a reference formulation of the stain, a lower specification limit formulation of the stain, an upper specification limit of the stain, etc. In some instances, the reference peak to which a measured peak is compared is an earlier measurement of the same stain or same stain formulation including e.g., where the stability and/or instability (e.g., degradation) of the peak is assessed over time.

In certain instances, a relative position of the peak may be described in terms of shift or spectral shift. As used herein, the terms "shift" or "spectral shift" as they relate to absorbance peaks refers to the difference in a measured spectral peak position as compared to a reference peak position. Spectral shift may also, in some instances, refer to shifts to greater or lesser absorbance with or without a change in the peak absorbance position of the peak. As such, spectral shifts encompassed within the described term include but are not limited to e.g., a positive shift (a shift to longer wavelength), a negative shift (a shift to a shorter wavelength) and combinations thereof. In some instances, a shift may be described in relationship to the color of the wavelength of light towards which the shift is observed including e.g., a far red shift, a red shift, an orange shift, a yellow shift, a green shift, a blue shift, a violet shift, an ultraviolet shift, etc.

Spectral shift may be represent an increase (i.e., positive shift, a shift to longer wavelength, etc.) or decrease (negative shift, t, a shift to a shorter wavelength, etc.) in wavelength as compared to the reference wavelength. The amount of spectral shift will depend on the formulation of a specific histological stain and the reference peak to which it is compared. As such, spectral shift of a measured peak may range from less than −10 nm to 10 nm or more including but not limited to e.g., −10 nm to 10 nm, −10 nm to 9 nm, −10 nm to 8 nm, −10 nm to 7 nm, −10 nm to 6 nm, −10 nm to 5 nm, −10 nm to 4 nm, −10 nm to 3 nm, −10 nm to 2 nm, −10 nm to 1 nm, −9 nm to 10 nm, −8 nm to 10 nm, −7 nm to 10 nm, −6 nm to 10 nm, −5 nm to 10 nm, −4 nm to 10 nm, −3 nm to 10 nm, −2 nm to 10 nm, −1 nm to 10 nm, −9 nm to 9 nm, −8 nm to 8 nm, −7 nm to 7 nm, −6 nm to 6 nm, −5 nm to 5 nm, −4 nm to 4 nm, −3 nm to 3 nm, −2 nm to 2 nm, −1 nm to 1 nm, 0 nm to 1 nm, −1 nm to 0 nm, and the like. Spectral shift will generally have an upper limit of ±20 nm or less including but not limited to e.g., ±19 nm or less, ±18 nm or less, ±17 nm or less, ±16 nm or less, ±15 nm or less, ±14 nm or less, ±13 nm or less, ±12 nm or less, ±11 nm or less or ±10 nm or less. Spectral shift will generally have a lower limit of ±1 nm or more.

In some instances, the spectra shift of a measured peak may be −10 nm, −9 nm, −8 nm, −7 nm, −6 nm, −5 nm, −4 nm, −3 nm, −2 nm, −1 nm, 1 nm, 2 nm, 3 nm, 4 nm, 5 nm, 6 nm, 7 nm, 8 nm, 9 nm or 10 nm.

In some instances, the position of the peak may be expressed relative to an absorbance peak, e.g., a measured or an expected absorbance peak, of a component of the stain or spectral shift may be calculated using an absorbance peak, e.g., a measured or an expected absorbance peak, of a component of the stain. For example, a stain formulation having two or more stain components may have an absorbance peak that is expressed relative to one component of the stain. As discussed above, the individual components of the stain affect the overall spectral characteristics of the stain such that the absorbance peaks of a stain formulation may be different from the absorbance peaks of individual components of the stain. For example, a peak of a stain formulation may be 1 or more nanometer (nm), up to and including 20 nm, different from the expected or measured peak of a component of the stain, including but not limited to e.g., more than 1 nm different, more than 2 nm different, more than 3 nm different, more than 4 nm different, more than 5 nm different, more than 6 nm different, more than 7 nm different, more than 8 nm different, more than 9 nm different, more than 10 nm different, etc.

In some instances, a peak of a stain formulation may have a spectral shift from an expected or measured peak of a component of the stain ranging from −10 nm to 10 nm including but not limited to e.g., −10 nm to 9 nm, −10 nm to 8 nm, −10 nm to 7 nm, −10 nm to 6 nm, −10 nm to 5 nm, −10 nm to 4 nm, −10 nm to 3 nm, −10 nm to 2 nm, −10 nm to 1 nm, −9 nm to 10 nm, −8 nm to 10 nm, −7 nm to 10 nm, −6 nm to 10 nm, −5 nm to 10 nm, −4 nm to 10 nm, −3 nm to 10 nm, −2 nm to 10 nm, −1 nm to 10 nm, −9 nm to 9 nm, −8 nm to 8 nm, −7 nm to 7 nm, −6 nm to 6 nm, −5 nm to 5 nm, −4 nm to 4 nm, −3 nm to 3 nm, −2 nm to 2 nm, −1 nm to 1 nm, 0 nm to 1 nm, −1 nm to 0 nm, and the like.

In some instances, a peak of a stain formulation may have a spectral shift from an expected or measured peak of a component of the stain of −10 nm, −9 nm, −8 nm, −7 nm, −6 nm, −5 nm, −4 nm, −3 nm, −2 nm, −1 nm, 1 nm, 2 nm, 3 nm, 4 nm, 5 nm, 6 nm, 7 nm, 8 nm, 9 nm or 10 nm.

In some instances, a specific spectral characteristic of a particular histological stain or stain formulation may be a width of one or more peaks obtained by measuring an absorbance spectrum of the histological stain on a spectrophotometer. Any convenient peak width measurement may find use as a specific spectral characteristic of a particular histological stain or stain formulation provided the width measurement sufficiently differentiates the histological stain or stain formulation. For example, peak width may be measured at any convenient absorbance value provided the peak width at the chosen absorbance value differentiates the histological stain or stain formulation from other histological stains or stain formulations.

Figure 7A:
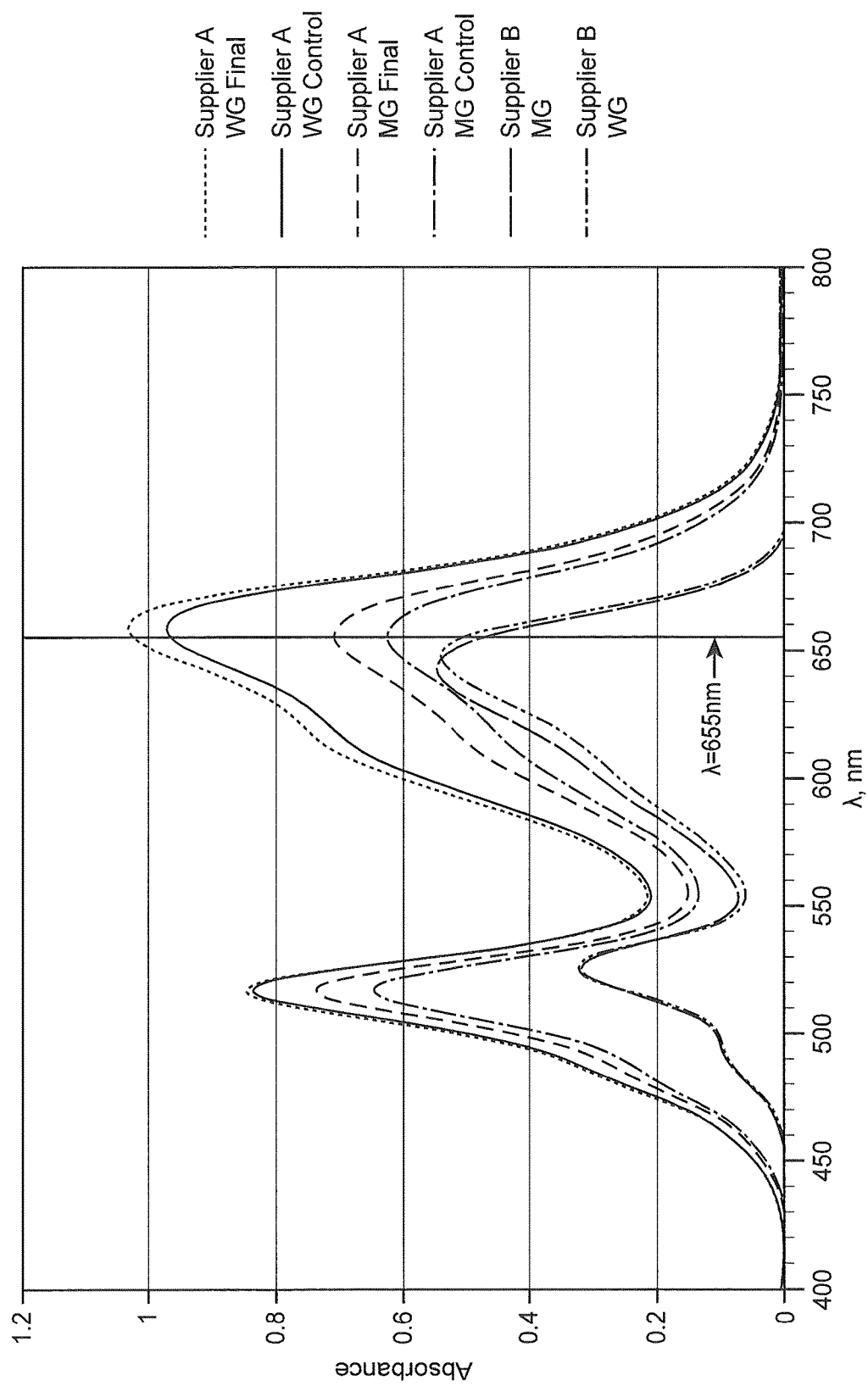
FIGS. 7A and 7B depicts the spectra for WG and MG stains from different suppliers showing the distinct spectral positions of absorbance peaks due to slightly different formulations.

Peak width measurements may be absolute or relative depending on the measurement performed, the spectra acquired, the comparison to be made, etc. For example, absolute peak width measurements may be expressed in terms of wavelengths measured in nanometers (nm) and may be calculated based on the difference between the wavelength at the first edge of the peak and the wavelength at the second edge of peak at a particular absorbance level. For example, a peak width of X nm may be calculated at absorbance Y for the first peak by determining the difference between the wavelength at the first edge of the peak and the wavelength at the second edge of the peak at absorbance value Y. Similar calculations may be performed for any peak or combinations of peaks of a spectrum at various absorbance values. In some instances, determination of peak width is facilitated by overlaying various spectra of different stains and/or different stain formulations, e.g., as depicted in FIG. 7A. An ordinary skilled artisan will readily understand that peak width may be calculated and compared for two or more peaks from one or more spectra regardless of whether the spectra are overlaid.

As the shape of individual peaks within a spectrum will vary with different stains, different formulations, different assay conditions, etc. the optimal absorbance at which peak width is calculated will also vary. In some instances, the absorbance may be based on the actual measured absorbance of the peak, e.g., the raw absorbance value returned by the spectrophotometer. In other instances, the absorbance may be based on relative absorbance of the peak, e.g. expressed as a proportion of the maximum absorbance of the peak, including but not limited to e.g., 10% maximum absorbance, 20% maximum absorbance, 25% maximum absorbance, 30% maximum absorbance, 40% maximum absorbance, 50% maximum absorbance (i.e., half-maximum absorbance), 60% maximum absorbance, 70% maximum absorbance, 75% maximum absorbance, 80% maximum absorbance, 90% maximum absorbance, etc. An ordinary skilled artisan will readily understand that, where comparisons between peak width measurements are made for two peaks having different maximum absorbance values, actual measured absorbance of the peaks, relative absorbance of the peaks or some normalization of the actual or relative absorbance of the peaks may be used depending on the particular context of the measurements.

In some instances, a specific spectral characteristic of a particular histological stain or stain formulation may be a peak absorbance value obtained by measuring an absorbance spectrum of the histological stain on a spectrophotometer. In some instances, the peak absorbance value may be based on the actual measured absorbance of the peak, e.g., the raw absorbance value returned by the spectrophotometer at various wavelengths. In other instances, the peak absorbance value may be based on relative absorbance of the peak, e.g. expressed as proportional absorbance as compared to a reference sample including e.g., the maximum absorbance of the reference sample (e.g., a "blank" sample, a "known" sample, a "reference standard", the absorbance of a validated stain, etc.). For example, a relative peak absorbance value may be expressed as a proportion of the a measured or stored reference value including but not limited to e.g., 10% reference absorbance, 20% reference absorbance, 25% reference absorbance, 30% reference absorbance, 40% reference absorbance, 50% reference absorbance, 60% reference absorbance, 70% reference absorbance, 75% reference absorbance, 80% reference absorbance, 90% reference absorbance, etc. An ordinary skilled artisan will readily understand that, where comparisons between peak absorbance values are made for two peaks having different maximum absorbance peak positions, actual measured peak absorbance values of the peaks, relative peak absorbance values of the peaks or some normalization of the actual or relative peak absorbance values of the peaks may be used depending on the particular context of the measurements. Accordingly, in some instances, the measured difference between two peak absorbance values for corresponding peaks from two different stains, two different stain formulations, or the same stain acquired at different times may be used in an assessment as described herein.

Specific spectral characteristic will generally be measured over a defined spectral range. In some instances, the defined spectral range may include all of the wavelength measurements obtained from the spectrophotometer (i.e., the total spectrum). In other instances, the defined spectral range may include a portion of the wavelength measurements obtained from the spectrophotometer (i.e., a partial spectrum). The spectra range may be predefined, e.g., based on a known spectral range where discriminating spectral characteristics are expected, or may be determined following total spectrum scans of two or more stains to be compared. In some instances, a predefined range may be used for an initial measurement and one or more subsequent ranges may be used following the initial measurement, e.g., where the initial measurement triggers the use of one or more subsequent ranges.

Useful spectral ranges will vary depending on the specific stains and/or stain formulations to be differentiated and the position(s) of discriminating spectral characteristics within the spectra. As such, spectral ranges over which absorbance is measured according to the methods as described herein may range from about 200 nm or less to about 800 nm or more including but not limited to e.g., 200 nm to 800 nm, 200 nm to 700 nm, 200 nm to 600 nm, 200 nm to 500 nm, 200 nm to 400 nm, 300 nm to 800 nm, 300 nm to 700 nm, 300 nm to 600 nm, 300 nm to 500 nm, 300 nm to 400 nm, 400 nm to 800 nm, 400 nm to 700 nm, 400 nm to 600 nm, 400 nm to 500 nm, 500 nm to 800 nm, 500 nm to 700 nm, 500 nm to 600 nm, 500 nm to 550 nm, 600 nm to 800 nm, 600 nm to 700 nm, 600 nm to 670 nm, 640 nm to 700 nm, 640 nm to 670 nm, and the like.

As will be understood by the ordinary skilled artisan, the resolution of the measured spectra will be of sufficient resolution to discriminate the spectral characteristics of two or more stains and/or two or more stain formulations. Accordingly, the required spectral resolution will depend upon the assessment to be made and the spectral characteristic(s) to be measured. For example, in some instances where the spectral characteristics between two stains or two stain formulations to be discriminated differ in wavelength, e.g., by 2 nm or less, the spectral resolution will be at least 1 nm or less. Accordingly, any appropriate spectral resolution may be employed provided the resolution is sufficient to make the desired discrimination. Thus, appropriate spectral resolutions may include but are not limited to e.g., at least 10 nm, at least 9 nm at least 8 nm, at least 7 nm, at least 6 nm, at least 5 nm, at least 4 nm, at least 3 nm, at least 2 nm, at least 1.0 nm, and the like.

In some instances, a spectral characteristic is obtained at specific wavelength without the use of a spectral range. For example, a predetermined specific wavelength, e.g., based on a known wavelength where discriminating spectral characteristics are expected, may be used to obtain absorbance data useful in making an assessment as described herein.

Spectrophotometers

Any convenient spectrophotometer may find use in making spectrophotometric measurements according to the methods as described herein provided the spectrophotometer is suitable for measuring absorbance over a spectrum range within which discriminatory spectrophotometric characteristics of the subject stain exist. At a minimum, a suitable spectrophotometer for use in the described methods will include a light source capable of generating light suitable for a spectrophotometric measurement, a sample analysis region configured to position the sample in the path of light generated from the light source and a detector suitable to detect the light generated from the light source that passes through the sample (e.g., a photodiode). In addition, a suitable spectrophotometer may also include additional optical components for manipulation of light, e.g., manipulation of the generated light before passing through the sample (e.g., a filter, a collimator, a polarizer, a mirror (e.g., a dichroic mirror), a prism, a lens, etc.) or manipulation of the light transmitted through the sample (e.g., a mirror, an amplifier, etc.). Detection of the signal within the spectrophotometer generally involves the conversion of the optical signal (e.g., the light transmitted through the sample) into an electrical signal such that the result of the measurement may be displayed (e.g., on a digital display), stored in electronic memory, or otherwise provided for a user (e.g., printed to a paper report) or conveyed to other downstream components.

In some instances, the method may include the use of an external spectrophotometer for measuring the absorbance spectrum of the histological stain. By "external" is meant that the spectrophotometer is not within the histology analyzer.

In certain embodiments, an external spectrophotometer may be a stand-alone spectrophotometer. Any convenient stand-alone spectrophotometer may find use in the methods as described herein provided the stand-alone spectrophotometer is capable of making absorbance measurements across the appropriate spectral range(s). For example, in some instances, suitable stand-alone spectrophotometers will include but are not limited to e.g., those commercially available from such supplier as: ABB (www(dot)abb(dot)com), Agilent (www(dot)agilent(dot)com), Analytik Jena (www(dot)analytik-jena(dot)com), Aurora Biomed (www(dot)aurorabiomed(dot)com), B&W Tek (www(dot)bwtek(dot)com), BaySpec (www(dot)bayspec(dot)com), Beckman Coulter (www(dot)beckmancoulter(dot)com), Biochrom (www(dot)biochrom(dot)co(dot)uk), BioTek (www(dot)biotek(dot)com), Bruker (www(dot)bruker(dot)com), Buck Scientific (www(dot)bucksci(dot)com), BWB Technologies (www(dot)bwbtech(dot)com), Cecil Instruments (www(dot)cecilinstruments(dot)com), CRAIC (www(dot)microspectra(dot)com), Eppendorf (www(dot)eppendorfna(dot)com), GBC Scientific (www(dot)gbcscientific(dot)com), GE Healthcare (www(dot)gelifesciences(dot)com), Hach (www(dot)hach(dot)com), Hamamatsu Photonics (www(dot)hamamatsu(dot)com), Hitachi High Technologies (www(dot)hitachi-hta(dot)com), HORIBA Scientific (www(dot)horiba(dot)com/scientific), JASCO (www(dot)jascoinc(dot)com), Malvern Instruments (www(dot)malvern(dot)com), Newport (www(dot)newport(dot)com), Ocean Optics (www(dot)oceanoptics(dot)com), PerkinElmer (www(dot)perkinelmer(dot)com), Renishaw (www(dot)renishaw(dot)com), Rigaku Raman (www(dot)rigakuraman(dot)com), SciAps (http(colon)//sciaps(dot)com), S.I. Photonics (www(dot)si-photonics(dot)com), Shimadzu (www(dot)shimadzu(dot)com), Tec5USA (www(dot)tec5usa(dot)com), Thermo Fisher Scientific (www(dot)thermoscientific(dot)com), and the like.

In some instances, the method may include the use of an internal spectrophotometer for measuring the absorbance spectrum of the histological stain. By "internal" is meant that the spectrophotometer is within the histology analyzer. In such instances, an internal spectrophotometer may share one or more components of the histology analyzer, meaning the histology analyzer and the spectrophotometer both use the common component in one or more processes while performing their normal functions. Shared components between an internal spectrophotometer and the histology analyzer housing the internal spectrophotometer may vary and may in some instances include but are not limited to e.g., reagents, liquid or sample handling components, power source components, reagent storage components, data transfer components, data storage components, data processing components, data output components, display components, user interface components, etc. An internal spectrophotometer may, in some instances, be assembled from commercially available components provided the assembled spectrophotometer is capable of making absorbance measurements across the appropriate spectral range(s).

Useful external spectrophotometers or components thereof (e.g., for use in an internal spectrophotometer) may include those spectrophotometers commercially available from e.g., Hitachi (including e.g., models U-0080D, U-1900, U-2900/2910, U-3900/3900H, etc. or components thereof), Analytik Jena AG (including e.g., models SPECORD 200/250/50/40/S 600/S 300 UV VIS, SPEK 2000, SPEKOL 1300, etc. or components thereof), PerkinElmer (including e.g., models LAMBDA 1050, 950, 850, 750, 650, 25, 35, 45, XLS, XLS+, etc. or components thereof), Varian (including e.g., models Cary 4000, Cary 100, Cary 5000, Cary 6000i, etc. or components thereof), BioTek Instruments (including e.g., models Epoch Microplate Spectrophotometer, PowerWaveXS, PowerWaveHT, etc. or components thereof), Cecil Instruments (including e.g., models Series 1000 UV/Visible, Super Aurius, Aurius UV/Visable, BioQuest, GeneQuest, DietQuest, ReflectaScan Reflectance, Aquarius, AquaQuest, etc. or components thereof), Shimadzu (including e.g., models UVmini-1240, UV-2550, UV-1800, UV-3600, etc. or components thereof), Jasco (including e.g., models V-660, V650, V630, V-670 etc. or components thereof), Thermo Scientific (including e.g., models NanoDrop 2000c, 2000, 8000, etc. or components thereof), S. I. Photonics (including e.g., models 420, 440, etc. or components thereof), Hach (including e.g., model DR 5000 or components thereof), Beckman Coulter (including e.g., models DU 800, DU 720/730, etc. or components thereof), Agilent (including e.g., model no. 8453 UV-Vis Spectrophotometer or components thereof), Jenway (including e.g., model nos. 6800, 6705, 6715, etc. or components thereof), Aurora (including e.g., model no. UV-VIS 230 or components thereof), and the like.

In some instances, external spectrophotometers, including components thereof, and/or internal spectrophotometers or components thereof may include, in part of in whole, those spectrophotometers and related components described in U.S. Pat. Nos. 8,638,433; 8,502,969; 8,189,199; 8,115,922; 8,049,884; 7,932,095; 7,787,120; 7,359,049; 7,262,844; 6,643,016; 5,162,868, and the like; the disclosures of which are incorporated herein by reference in their entirety.

Prior to measuring a spectrum of a histological stain on a spectrophotometer the histological stain or a sample thereof may be prepared for analysis. Preparation for analysis of a stain or a sample thereof may include transferring an aliquot of the stain to an analysis vessel that is compatible with the spectrophotometer. Compatible analysis vessels will vary depending on the particular spectrophotometer employed and the volume of the sample to be tested. In some instances, suitable analysis vessels include are not limited to e.g., a cuvette, a capillary and a multi-well plate. Accordingly, transfer of the aliquot to the analysis vessel may be performed by any suitable method including but not limited to, e.g., pipetting the sample into the vessel, pumping the sample into or through the vessel (e.g., through positive pressure), transfer of the sample through capillary action, transfer of the sample through negative pressure, transfer of the sample through gravity, etc.

In some instances, the sample may be diluted before, during, or after transfer into the analysis vessel. For example, in some instances an appropriate diluent may be added to the sample prior to transfer into the analysis vessel including but not limited to e.g., in a dilution vessel or mixing vessel. In some instances a suitable diluent may be added to the sample during transfer into the analysis vessel including but not limited to e.g., where an appropriate diluent is present in the analysis vessel prior to addition of the sample and the sample is diluted upon mixing with the diluent in the analysis vessel. In some instances a suitable diluent may be added to the sample after transfer into the analysis vessel including but not limited to e.g., where the sample is added to an empty analysis vessel and an appropriate diluent is added to the analysis vessel after the sample is present.

Appropriate diluents will vary depending on the nature of the spectroscopic measurement to be performed and the specific histological stain to be analyzed. For example, in some instances an appropriate diluent may be an aqueous solvent including but not limited to e.g., water, phosphate buffered saline (PBS), tris-buffered saline (TBS), and the like. In some instances an appropriate diluent may be an organic solvent including but not limited to e.g., ethanol, methanol, isopropanol, chloroform, and the like. In some instances, an appropriate diluent may be the primary solvent of the stain to be analyzed.

Any convenient dilution may find use in the methods as described herein provided the dilution allows for spectrophotometric detection of distinguishing spectral characteristics when the diluted stain is measured on a spectrophotometer. Appropriate dilutions will vary depending on the starting concentration of the stain, the volume of the aliquot to be analyzed, the particular spectrophotometer to be used, etc. In some instances, appropriate dilutions may include but are not limited to e.g., about 1:1, about 1:2, about 1:4, about 1:5, about 1:10, about 1:15, about 1:20, about 1:25, about 1:30, about 1:40, about 1:50, about 1:60, about 1:70, about 1:75, about 1:80, about 1:90, about 1:100, about 1:150, about 1:200, about 1:250, about 1:300, about 1:400, about 1:500, about 1:600, about 1:700, about 1:750, about 1:800, about 1:900, about 1:1000, about 1:1500, about 1:2000, and the like.

In some instances, the method may include to preparation of two or more dilutions or a dilution series prior to absorbance measurements on a spectrophotometer to produce a plurality of absorbance spectra for the histological stain at the two or more dilutions.

Histological Stains

The instant disclosure includes methods of assessing a histological stain used in a histology analyzer by measuring the absorbance spectrum of the histological stain on a spectrophotometer. As used herein, histology stains refer to those stains used in microscopic analysis of the cellular anatomy and/or morphology of cells obtained from a multicellular organism. Histology stains generally include at least one dye that stains one or more cell types and/or components of one or more cell types a contrasting color. Histology stains may also include at least one counter-stain that stains the rest of the cells or the rest of the cell a different color. Histological techniques, stains and staining methods are well-known and include but are not limited to those described in Kiernan. *Histological and histochemical methods: Theory and practice*. Oxford: Butterworth/Heinemann, 1999 and Bancroft & Stevens. *Theory and practice of histological techniques*. New York, N.Y.: Churchill Livingstone, 1996; the disclosures of which are incorporated herein by reference in their entirety.

Histological staining techniques can be specific, staining one or more particular cells in a specific way, or non-specific, staining essentially all cells or most cells in the same or similar way. Histology stains include but are not limited to e.g., Alcian blue stains, Aniline blue stains, Azan stains, Biebrich scarlet-acid fuchsin stains, Carbol-fuchsin stains, Chrome alum/haemotoxylin stains, Congo Red stains, Crystal violet stains, Fast Red stains, Hematoxylin and Eosin (H&E) stains, Iron Hematoxylin stains, Isamin blue/eosin stains, Jenner's stains, Mallory's Phosphotungstic Acid Hematoxylin (PTAH) stains, Mallory's Trichrome stains, Masson stains, Malachite Green stains, Methyl Green-Pyronin (MGP) stains, Nissl and methylene blue stains, Nissl stains, Oil Red O stains, Orcein stains, Osmic Acid stains, Osmium Tetroxide stains, Papanicolaou stains, Periodic Acid-Schiff (PAS) stains, Reticulin stains, Romanowsky stains, Safranin O stains, Silver stains, Sudan Black and osmium stains, Toluidine-blue stains, Trichrome AB, Trichrome LG, Trypan Blue stains, van Gieson stains, Verhoff's stains, Weigert's resorcin-fuchsin stains, and the like.

Dyes included in histology stains will vary depending on the stain formulation and the desired staining result. In some instances, dyes useful in histology stains may include but are not limited to, e.g., Acid Fuchsin calcium salt, Acid fuschin, Alcian Blue, Alizarin Red, Aniline blue, Aniline Blue diammonium salt, Auramine O Dye, Azure, Azure A chloride, Azure B, Basic Fuchsin, Bismarck Brown Y, Brilliant Cresyl Blue, Brilliant Green, Carmine, Congo Red, Cresyl Violet acetate, Crystal Violet, Darrow Red, Eosin, Eosin B, Eosin Y, Eosin Y disodium salt, Erythrosin B, Erythrosin extra bluish, Ethyl eosin, Fast Green FCF, Hematoxylin, Indigo carmine, Janus Green B, Light Green SF Yellowish, Malachite Green oxalate salt, Methyl Blue, Methyl green, Methyl Green zinc chloride, Methyl Orange, Methyl violet 2B, Methylene blue, Methylene Violet (Bernthsen), Neutral Red, Nigrosin, Nile Blue A, Oil Red O, Orange G, Orange II sodium salt, Orcein synthetic, Phloxine B Dye, Pyronin B, pyronin G, Pyronin Y, Resazurin sodium salt, Rose Bengal sodium salt, Safranin O, Sudan Black B, Sudan III, Sudan IV, Thionin acetate salt, toluidine, Toluidine Blue O, and the like.

In some instances, histological stains assessed in the subject methods include Romanowsky stains. Romanowsky stains are generally neutral stains composed of various components including but not limited to methylene blue (e.g., Azure B) and eosin (e.g., Eosin Y) dyes. Azures are basic dyes that bind acid nuclei and result in a blue to purple color. Eosin is an acid dye that is attracted to the alkaline cytoplasm producing red coloration. Romanowsky stains vary and include various formulations including those containing various azure and eosin analogs. Romanowsky stains and their mechanisms of staining are well-known and described in e.g., Horobin & Walter. *Histochemistry* (1987) 86:331-336; Marshall et al. *J Clin Pathol* (1978) 31(3):280-2; Marshall et al. *J Clin Pathol*. (1975) 28(11):920-3; *J Clin Pathol* (1975) 28(8):680-5; the disclosures of which are incorporated herein by reference.

Romanowsky stains include but are not limited to Giemsa Stain, Wright Stain, Wright Giemsa Stain, Jenner Stain, Jenner-Giemsa Stain, Leishman Stain, May Grunwald Stain, May Grunwals Giemsa Stain, and the like. Each Romanowsky stain may exist in various formulations either as derived from various different recipes or as supplied from various providers. Romanowsky stain formulations may include various stain components including but not limited to e.g., methylene blue, azure A, azure B, azure C, toluidine blue, thionine, methylene violet Bernthsen, methyl thionoline, thionoline, eosin, eosin Y, tribromofluorescein, fluorescein, thiazine dyes, and the like. Romanowsky stain formulations may include various solvents to dissolve stain components including aqueous and organic solvents including but not limited to e.g., water and alcohols including but not limited to e.g., methanol, ethanol, isopropyl alcohol, etc.

Without being bound by theory, the particular ratios of components (including dye components, solvents, etc.) of Romanowsky stains, and histological stains in general, are considered to influence the interaction of the stain components to produce the particular coloring of cells prepared with each stain. The color resulting from a stain formulation is the result of these interactions and is therefore more complex than the simple additive result of the individual components. The instant disclosure describes how it was discovered that these complex interactions lead to shifts in the absorbance peaks of the individual components of the stains resulting in a peak profile that is specific to each stain formulation. Accordingly, even very similar stains, including e.g., those that cannot be differentiated by the human eye and those stains of the same type but from different manufactures, may be differentiated based on the spectroscopic methods described.

In some instances, the histology stains to be assessed or differentiated include Romanowsky stains including but not limited to e.g., Wright Giemsa, May Grunwald and May Grunwals Giemsa. The histology stains assessed include hematological stains, cytological stains and the like. The histological stains of the instant disclosure include those stains used in a histology analyzer including e.g., an automated histology analyzer, an automated cytology analyzer, an automated hematological analyzer, etc. Histology analyzers of the instant disclosure include but are not limited to e.g., those commercially available from Abbott Laboratories and/or Abbott Diagnostics (including e.g., the CELL-DYN systems, and the like), from Sysmex (including e.g., the Sysmex DI60, CellaVision DM1200, and the CellaVision DM 9600 systems and the like), from MEDICA (including e.g., the EasyCell systems, and the like), from Horiba (including e.g., the Pentra and Micros systems, and the like), from Siemens (including e.g., the ADVIA and Kematek systems, and the like), from Beckman Coulter (including e.g., the UniCel systems, and the like), etc.

The histological stains and components thereof include those commercially available from such suppliers including not limited to e.g., Sigma Aldrich, Thermo Fisher Scientific, Avantor Proformance Materials, VWR International, Polysciences Inc., and the like.

Libraries

The instant disclosure includes methods of assessing a histological stain by measuring the absorbance spectrum of the histology stain and comparing one or more spectral characteristics of the histology stain to a library of spectral characteristics for a number of histology stains and/or histology stain formulations. The libraries described herein may include any or all spectral characteristics for any or all histological stains. In some instances, the libraries described herein will include but are not limited to any or all of the spectral characteristics described herein for any or all histological stains described herein or formulations thereof.

At a minimum a library for assessing a histological stain will include two or more histological stains or stain formulations and one or more corresponding spectral characteristics of the two or more histological stains or stain formulations. The number of histological stains represented in the library will vary depending e.g., on the desired use of the library and/or the particular histology analyzer, and may range from 1 to about 50 including but not limited to e.g., 1 to 50, 1 to 40, 1 to 30, 1 to 29, 1 to 28, 1 to 27, 1 to 26, 1 to 25, 1 to 24, 1 to 23, 1 to 22, 1 to 21, 1 to 20, 1 to 19, 1 to 18, 1 to 17, 1 to 16, 1 to 15, 1 to 14, 1 to 13, 1 to 12, 1 to 11, 1 to 10, 1 to 9, 1 to 8, 1 to 7, 1 to 6, 1 to 5, 1 to 4, 1 to 3, etc.

The number of histological stain formulation for each histological stain represented in the library will vary depending e.g., on the desired stain and/or the particular histology analyzer, and may range from 1 to about 20 including but not limited to e.g., 1 to 20, 1 to 19, 1 to 18, 1 to 17, 1 to 16, 1 to 15, 1 to 14, 1 to 13, 1 to 12, 1 to 11, 1 to 10, 1 to 9, 1 to 8, 1 to 7, 1 to 6, 1 to 5, 1 to 4, 1 to 3, etc.

The number of different spectral characteristics for each histological stain or each stain formulation represented in the library will vary depending e.g., on the desired stain, the desired formulation and/or the particular histology analyzer, and may range from 1 to about 10 including but not limited to e.g., 1 to 10, 1 to 9, 1 to 8, 1 to 7, 1 to 6, 1 to 5, 1 to 4, 1 to 3, etc. In some instances, number of different spectral characteristics for each histological stain or each stain formulation represented in the library will be 10 or less including but not limited to 9 or less, 8 or less, 7 or less, 6 or less, 5 or less, 4 or less, 3 or less, 2 or less, or may be 1. In some instances, number of different spectral characteristics for each histological stain or each stain formulation represented in the library will be 1 or more including but not limited to 2 or more, 3 or more, 4 or more, 5 or more, 6 or more, 7 or more, 8 or more, 9 or more, 10 or more, etc. Each different spectral characteristic may be represented by various individual values depending on the number of peaks or the number of different measurements taken for each peak.

In some instances, the library will include values corresponding to the position of one or more peaks of a plurality of histological stains or formulations thereof. In some instances, the library will include values corresponding to the width (including e.g., peak-width-at-half-maximum-absorbance) of one or more peaks of a plurality of histological stains or formulations thereof. In some instances, the library will include values corresponding to the peak absorbance of one or more peaks of a plurality of histological stains or formulations thereof. In some instances, the library will include values corresponding to relative peak characteristics of a plurality of histological stains or formulations thereof. In some instances, the library will include values corresponding to the spectral shifts of a plurality of histological stains or formulations thereof. In some instances, the library will include a combination of values including but not limited to e.g., a combination of values corresponding to the position of one or more peaks, values corresponding to the width of one or more peaks, values corresponding to the peak absorbance of one or more peaks, values corresponding to relative peak characteristics, values corresponding to the spectral shifts or sub-combinations thereof.

In some instances, the library values for the plurality of histological stains or formulations thereof will be total spectrum values, meaning the values are not limited by spectra range and include values across the entire measurable spectrum. In other instances, the library values for the plurality of histological stains or formulations thereof will be spectrum range values, meaning the values are limited to a particular spectral range including from about 200 nm or less to about 800 nm or more including but not limited to e.g., 200 nm to 800 nm, 200 nm to 700 nm, 200 nm to 600 nm, 200 nm to 500 nm, 200 nm to 400 nm, 300 nm to 800 nm, 300 nm to 700 nm, 300 nm to 600 nm, 300 nm to 500 nm, 300 nm to 400 nm, 400 nm to 800 nm, 400 nm to 700 nm, 400 nm to 600 nm, 400 nm to 500 nm, 500 nm to 800 nm, 500 nm to 700 nm, 500 nm to 600 nm, 500 nm to 550 nm, 600 nm to 800 nm, 600 nm to 700 nm, 600 nm to 670 nm, 640 nm to 700 nm, 640 nm to 670 nm, and the like.

In some instances, the library is a library of Romanowsky stains spectral characteristics and includes one or more spectral characteristics for a plurality of Romanowsky stains including but not limited to e.g., Wright Giemsa, May Grunwald and May Grunwals Giemsa.

In some instances, the library will include one or more reference spectral characteristics for Wright Giemsa including but not limited to e.g., a reference value corresponding to the position of one or more Wright Giemsa peaks, a reference value corresponding to the width of one or more Wright Giemsa peaks, a reference value corresponding to the peak absorbance of one or more Wright Giemsa peaks, a reference value corresponding to a Wright Giemsa peak spectral shift, etc. In some instances, the library will include a reference wavelength peak of absorbance at essentially 659 nm for Wright Giemsa and/or the reference wavelength peaks of one or more individual component of the Wright Giemsa stain.

In some instances, the library will include one or more reference spectral characteristics for May Grunwald including but not limited to e.g., a reference value corresponding to the position of one or more May Grunwald peaks, a reference value corresponding to the width of one or more May Grunwald peaks, a reference value corresponding to the peak absorbance of one or more May Grunwald peaks, a reference value corresponding to a May Grunwald peak spectral shift, etc. In some instances, the library will include a reference wavelength peak of absorbance at essentially 656 nm for May Grunwald and/or the reference wavelength peaks of one or more individual component of the May Grunwald stain.

In some instances, the library will include one or more reference spectral characteristics for May Grunwals Giemsa including but not limited to e.g., a reference value corresponding to the position of one or more May Grunwals Giemsa peaks, a reference value corresponding to the width of one or more May Grunwals Giemsa peaks, a reference value corresponding to the peak absorbance of one or more May Grunwals Giemsa peaks, a reference value corresponding to a May Grunwals Giemsa peak spectral shift, etc.

In some instances, the library will include reference spectral characteristics for Wright Giemsa, May Grunwald and May Grunwals Giemsa including but not limited to e.g., a reference value corresponding to the position of one or more peaks for each of the three stains, a reference value corresponding to the width of one or more peaks for each of the three stains, a reference value corresponding to the peak absorbance of one or more peaks for each of the three stains, a reference value corresponding to a peak spectral shift for each of the three stains, etc.

In some instances, a library will include reference values corresponding to incorrect stain formulations. For example, in some instances a library may include formulations found to perform outside of specifications or formulations found to produce undesirable results. Such reference values for incorrect stain formulations may serve, in some instances, to provide boundaries or thresholds for particular assessments including but not limited to e.g., stain quality assessments.

In some instances, a library will include reference values corresponding to "expired" stains. By "expired" as used herein is meant to refer to a stain that at one point following formulation performed within specifications but at the time of use the stain no longer performs within specifications. A stain may expire by the passage of time and/or through storage in or exposure to conditions insufficient to sustain stain performance. For example, in some instances a library may include stains having been formulated and allowed to expire either through the passage of sufficient time or through inappropriate storage of the stain or other exposure of the stain to conditions, including environmental conditions, sufficient to alter the characteristics of the stain and negatively impact stain performance. Such reference values for expired stain formulations may serve, in some instances, to provide boundaries or thresholds for particular assessments including but not limited to e.g., stain quality assessments.

As described in more detail herein, libraries of the instant disclosure may be utilized in comparisons made to measured values to perform histology stain assessments. Libraries may be stored digitally on non-transitory computer readable medium and may be accessed by circuitry and/or a computing device to perform the methods as described herein.

Assessments

The instant disclosure includes assessments of histological stains used in a histology analyzer made using spectrophotometric methods. The assessments described herein are generally based on the comparison of one or more spectral characteristics from the measured absorbance spectrum of a subject histological stain with reference spectral characteristics contained in a library of such characteristics for a plurality of histological stains and/or stain formulations.

In some instances, the assessment is used to determine the identity of the subject histological stain. For example, a subject histological stain of unknown or assumed identity may be obtained and the absorbance spectrum of the stain may be determined by measuring the stain on a spectrophotometer. From the measured spectrum one or more spectral characteristics of the stain may be determined and compared to a reference value to determine the identity of the stain and/or confirm the identity of the stain.

In some instances, the comparing includes searching for an exact match to the one or more spectral characteristics and when an exact match is found the stain identity is returned or the assumed stain identity is confirmed. In other instances, the comparing includes searching for at least a near match to the one or more spectral characteristics and when at least a near match is found the stain identity is returned or the assumed stain identity is confirmed. By "near match" is meant that the match of the measured characteristics to the reference value is within a predetermined range including but not limited to e.g., within a predetermined percentage of the reference value (e.g., ±10%, ±9%, ±8%, ±7%, ±6%, ±5%, ±4%, ±3%, ±2%, ±1%, ±0.9%, ±0.8%, ±0.7%, ±0.6%, ±0.5%, ±0.4%, ±0.3%, ±0.2%, ±0.1%, etc.), within a standard deviation of the reference value or multiple or portion thereof (e.g., within two standard deviations, within one standard deviation, with 0.5 standard deviations, etc.), within the standard error of the mean, within a confidence interval (e.g., within the 99% confidence interval (CI), within the 98% CI, within the 97% CI, within the 96% CI, within the 95% CI, within the 94% CI, within the 93% CI, within the 92% CI, within the 91% CI, within the 90% CI, within the 85% CI, within the 80% CI, within the 75% CI, etc.), within a specified number of units from the reference value (e.g., within ±1 nm of a reference wavelength, within ±2 nm of a reference wavelength, within ±3 nm of a reference wavelength, within ±4 nm of a reference wavelength, within ±5 nm of a reference wavelength, etc.), and the like.

In some instances, the assessment may include the comparison of two or more different spectral characteristics and a match may be based on at least two of the different spectral characteristics being an exact match with the corresponding reference values. In some instances, the assessment may include the comparison of two or more different spectral characteristics and a match may be based on at least two of the different spectral characteristics being at least near matches with the corresponding reference values.

In some instances, the assessment is used to determine the identity of a Romanowsky stain. For example, a subject Romanowsky stain of unknown or assumed identity may be obtained and the absorbance spectrum of the stain may be determined by measuring the stain on a spectrophotometer. From the measured spectrum one or more spectral characteristics of the stain may be determined and compared to a reference value to determine the identity of the Romanowsky stain and/or confirm the identity of the Romanowsky stain. In some instances, the assessment determines whether the stain is Wright Giemsa. In some instances, the assessment determines whether the stain is May Grunwald. In some instances, the assessment determines whether the stain is May Grunwals Giemsa.

In some instances, the assessment of the identity of the subject histological stain includes identifying a particular formulation of the histological stain. The term "composition" and "formulation" as used herein to refer to histological stain compositions and formulations are used interchangeably and generally refer to the combined components of a particular histological stain and their specific amounts in relationship to one another. For example, two stains of the same type, e.g., two Romanowsky stains or two Giemsa stains, although of the same type, may have different compositions or formulations. Differing formulations may be prepared purposefully, e.g., from differing recipes or by the inclusion/exclusion of an additive, or may be prepared accidentally, e.g., by the inadvertent inclusion of an improper amount of a particular component or inadvertent inclusion/exclusion of an improper dye or other agent. Differing formulations may be due to various factors including but not limited to e.g., different formulations prepared by different manufactures, different formulations prepared by a single manufactures, preparation of a formulation that is outside of specification, improper processing during the formulation process (including e.g., improper dilution, improper filtration, improper heating, etc.), etc.

In some instances, an improper formulation may at some point have been a proper formulation and may have "expired" to become an improper formulation through other means including but not limited to e.g., contamination, evaporation, etc. As such, in some instances, an assessment to determine whether a stain is improperly formulated may also assess whether the stain has expired or has become an improper formulation or a formulation expected to perform outside of specifications.

In some instances, an assessment as described herein may be performed to determine the quality of the stain. For example, in some instances a stain of known identity or assumed identity may be assessed to determine if the stain is of sufficient or desired quality. In some instances, a stain of known identity or assumed identity may be obtained and the absorbance spectrum of the stain may be determined by measuring the stain on a spectrophotometer. From the measured spectrum one or more spectral characteristics of the stain may be determined and compared to a reference value to determine the quality of the stain and/or confirm the quality of the stain.

In some instances, the determining the quality of the stain include comparing the stain to one or more reference quality thresholds or ranges of a particular spectral characteristic. Reference quality thresholds and ranges of spectral characteristics can be determined by any convenient method. For example, in some instances, reference quality thresholds or ranges are determined by preparing a plurality of different stain formulations and testing the formulations for desired or undesired characteristics, identifying which formulations have the desired or undesired characteristics, determining the spectral characteristics for the formulations and correlating the presence or absence of the desired or undesired characteristics with the spectral characteristics of the formulations.

Such desired or undesired characteristics will vary any may include but are not limited to performance characteristics of the formulation in a histological assay. The performance characteristics of the formulation may be determined in an automated or manual histological assay. In some instances, the histological assay is a hematological assay including but not limited to e.g., a blood count, hematological screening of known specimens, etc. In some instances, desired performance characteristics of a histological or hematological assay include but are not limited to e.g., desired cell coloration, correct/incorrect cell identification, correct/incorrect cell classification, expert stain evaluation, expert stain scoring, etc. In some instances, the performance characteristics are evaluated for all of the cell types of the sample. In some instances the e performance characteristics are evaluated for specific cell types of the sample including but not limited to e.g., leukocytes, basophils, eosinophils, lymphocytes, monocytes, neutrophils, platelets, red blood cells, etc. In some instances, the performance characteristics of the formulation are assessed in a histological assay requiring a human expert to evaluate the performance characteristic. In some instances, the performance characteristics of the formulation are assessed in a histological assay performed e.g., using a histology analyzer performing a computer-based analysis. In some instances, an assay not requiring a human expert may be considered an unbiased assay to evaluate performance characteristics of the formulation.

The measured spectral characteristic may be compared to one or more reference quality thresholds or ranges by a variety of means including comparing the measured characteristic to the threshold or range and if the measured characteristic is above or below the threshold as desired or within the range then the stain quality is returned as adequate. In some instances, the quality range may be determined as values above and below a target value (e.g., a target value determined from spectral analysis of a target stain formulation). For example, a quality range may be within a predetermined percentage of the target value (e.g., ±10%, ±9%, ±8%, ±7%, ±6%, ±5%, ±4%, ±3%, ±2%, ±1%, ±0.9%, ±0.8%, ±0.7%, ±0.6%, ±0.5%, ±0.4%, ±0.3%, ±0.2%, ±0.1%, etc.), within a standard deviation of the target value or multiple or portion thereof (e.g., within two standard deviations, within one standard deviation, with 0.5 standard deviations, etc.), within the standard error of the mean, within a confidence interval (e.g., within the 99% confidence interval (CI), within the 98% CI, within the 97% CI, within the 96% CI, within the 95% CI, within the 94% CI, within the 93% CI, within the 92% CI, within the 91% CI, within the 90% CI, within the 85% CI, within the 80% CI, within the 75% CI, etc.), within a specified number of units from the target value (e.g., within ±1 nm of a target wavelength, within ±2 nm of a target wavelength, within ±3 nm of a target wavelength, within ±4 nm of a target wavelength, within ±5 nm of a target wavelength, etc.), and the like.

As such, in some instances stain quality is assessed based on the difference of the subject stain from a reference stain and where the subject stain is outside a reference range the subject stain is deemed to be of adequate quality. Adequate quality of a stain formulation may be assessed based on the presence or absence of desired or undesired characteristics and/or measured performance characteristics as described above.

In some instances, a quality threshold may be determined as a value at or above a target value where the target value is determined by assessing the performance and spectral characteristics for a plurality of stains or stain formulations and those formulations having adequate performance are those that measure at or above the target spectral value.

In some instances, the quality threshold may be determined as a value at or below a target value where the target value is determined by assessing the performance and spectral characteristics for a plurality of stains or stain formulations and those formulations having adequate performance are those that measure at or above the target spectral value.

In some instances, the quality of a histological stain may be assessed according to a predetermined time schedule, e.g., to identify when a stain is expired, to predict when a stain will perform adequately, to predict when a stain may perform outside of specifications, to predict when a stain may produce one or more undesirable performance characteristics, etc. The optimal frequency for assessing stain quality will vary and will depend on the particular stain and/or formulation, the storage conditions of the stain, etc. In some instances, the quality of the stain is assess at least annually, including but not limited to e.g., at least quarterly, at least semimonthly, at least monthly, at least bimonthly, at least weekly, at least biweekly, at least every two days, at least daily, etc.

In some instances, an assessment, including identity, quality or other assessments are performed on demand, e.g., as specified by a user. In other instances, an assessment is preformed prior to use of the histology analyzer within which the stain is used including but not limited to e.g., upon start-up of the histology analyzer, prior to running a sample on the histology analyzer, after running a predetermined number of samples (including but not limited to e.g., after running 5 samples, after running 10 samples, after running 20 samples, after running 50 samples, after running 100 samples, after running 500 samples, after running 1000 samples, etc.) on the histology analyzer, etc.

Devices and Systems

The instant disclosure includes spectrophotometric devices and systems for performing the methods for assessing histological stains used in a histology analyzer as described herein. Aspects of the devices systems include measuring spectrophotometric characteristics of a subject histological stain using a spectrophotometer configured to identify one or more characteristics that are specific to a particular stain and/or stain formulation.

The devices and systems configured to perform the methods described herein will generally include at least one spectrophotometer, a library of reference spectral characteristics for various histological stains or formulations thereof, and spectral processing circuitry. The components may be assembled in a single device or may be assembled as a system of components separated between in two or more devices. In some instances, a device, a system or components thereof may be external but near (i.e., attached to the external housing of or on the same working surface or within the same room or building, etc.) the histology analyzer that uses the assessed stain. In other instances, a device, a system or components thereof may be positioned internally (i.e., within, inside of, or housed within) the histology analyzer that uses the assessed stain.

Any convenient spectrophotometer, as described above, may find use in a device and/or system for making spectrophotometric measurements according to the methods as described herein provided the spectrophotometer is suitable for measuring absorbance over a spectrum range within which discriminatory spectrophotometric characteristics of the subject stain exist. Such spectrophotometers and components thereof are well-known. Suitable spectrophotometers and components thereof include but are not limited to e.g., those described herein.

In some instances, a system of the instant disclosure may include an absorbance analyzer or collectively an absorbance analyzer and a histology analyzer, where an absorbance analyzer includes at least a spectrophotometer and a means for storing measured spectra produced by the spectrophotometer. In some instances, an absorbance analyzer may also include a library of reference spectral characteristics for a plurality of histological stains and/or stain formulations. In some instances, an absorbance analyzer may also include spectra processing circuitry for performing one or more of identifying spectral characteristics from the measured spectra and/or comparing the measured spectral characteristics to reference spectral characteristics. In some instances, an absorbance analyzer may also include one or more removable computer-readable storage mediums for storing measured spectra, spectral characteristics, and/or the result of any analysis and/or comparisons.

In some instances, the devices and/or systems of the instant disclosure include a library for assessing a histological stain, as described above, including e.g., at least two or more histological stains or stain formulations and one or more corresponding spectral characteristics of the two or more histological stains or stain formulations. In many instances, the library will include a plurality of reference spectral characteristics for various histological stains and/or stain formulations. The library may be stored in the device or system, e.g., stored electronically on non-transitory computer readable medium or other computer memory. In some instances, the library may be removable and/or update-able such that spectral characteristics for new stains or formulations may be added by replacing the library and/or updating the library.

In some instances, the components of the systems as described herein may be connected by a wired data connection. Any suitable and appropriate wired data connection may find use in connecting the components of histology stain assessment systems, e.g., as described herein, including but not limited to e.g., commercially available cables such as a USB cable, a coaxial cable, a serial cable, a C2G or Cat2 cable, a Cat5/Cat5e/Cat6/Cat6a cable, a Token Ring Cable (Cat4), a VGA cable, a HDMI cable, a RCA cable, an optical fiber cable, and the like. In some instances, e.g., where data security is less of a concern, wireless data connections may be employed including but not limited to e.g., radio frequency connections (e.g., PAN/LAN/MAN/WAN wireless networking, UHF radio connections, etc.), an infrared data transmission connection, wireless optical data connections, and the like.

In some instances, the devices and/or systems of the instant disclosure include spectra processing circuitry. Such spectra processing circuitry may be programmed and/or contain instructions to perform one or more tasks related to processing the measured spectra received from the spectrophotometer. For example, in some instances, the spectra processing circuitry is programmed to identify one or more spectral characteristics, described above, from a measured spectrum received from the spectrophotometer. In some instances, the spectra processing circuitry is programmed to make a comparison between a measured spectral characteristic and a reference spectral characteristic, e.g., as stored in a library, to make an assessment according to the methods described herein.

In some instances, spectra processing circuitry may be programmed to, following the comparison, further determine the identity or quality of the subject histological stain. In instances where the identity of the stain is assessed, such determinations require the spectra processing circuitry to associate the result of the comparison with a library of spectral characteristics for various stains and/or stain formulations in order to identify a match (e.g., an exact match, a near match, a best match, etc.). In instances where the quality of the stain is assessed, such determinations require the spectra processing circuitry to associate the result of the comparison with one or more quality thresholds or ranges of spectral characteristics for the assumed or known stain identity in order to determine whether the subject stain is within a quality range or above or below a quality threshold.

In some instances, spectra processing circuitry may be programmed to incorporate into a comparison or assessment a user supplied criteria. For example, in some instances a user input my provide the assumed identity of the subject stain or an assumed quality of the subject stain and the spectra processing circuitry may be programmed to assess whether the user supplied data matches or correlates with the result of the assessment. In some instances, the spectra processing circuitry is configured or programmed to compare the assumed identity of the histological stain to the assessed identity of the histological stain and output a result as to whether the assumed identity and the assessed identity of the histological stain match. In some instances, the spectra processing circuitry is configured or programmed to compare the assumed quality of the histological stain to the assessed quality of the histological stain and output a result as to whether the quality of the histological stain is sufficient for use in a histological assay. In some instances, the stain is automatically assumed to be of sufficient quality to perform a histological assay unless indicated otherwise by a result from the spectra processing circuitry.

In some instances, the spectra processing circuitry is capable of triggering further functions of the device or system. For example, in some instances, the result of an assessment processed by the spectra processing circuitry results in triggering of a signaling system, e.g., to indicate to a user the result of the assessment (e.g., indicate the identity of the stain, indicate the quality of the stain, etc.). Such indications may be displayed on a user interface or may be reported by a singling system including but not limited to e.g., an alarm, an indicator light, etc. In other instances, the result of an assessment processed by the spectra processing circuitry results in triggering of additional spectral measurements of the sample. In some instances, the result of an assessment processed by the spectra processing circuitry results in triggering of the ejection of the subject stain or a termination of a requested histological assay using the subject stain, e.g., where the subject stain is determined not to be of the assumed identity or of sufficient quality.

In some instances, the devices and systems as described herein further include a signal system where the signal system may be configured to report the result of the assessment. Such signal systems will vary depending on the particular configuration of the device and or system and may include but are not limited to e.g., an alarm, an indicator light, a display (e.g., a computer monitor, a graphical user interface (GUI), etc.), a printer configured to print, e.g., onto tangible media (including e.g., paper or tape), and the like. In some instances, the signal system indicates, e.g., sounds, lights up, or otherwise displays, to a user when the assumed identity and the assessed identity of the histological stain do not match. In some instances, the signal system indicates, e.g., sounds, lights up, or otherwise displays, to a user when the quality of the assessed stain is above or below a quality threshold or within or outside of a quality range.

In some instances, the spectra processing circuitry is capable of triggering further functions of the device or system that are not dependent on the result of the assessment. For example, in some instances, the spectra processing circuitry is configured to trigger the device or system to perform assessments of a histological stain according to a predetermined time schedule. In some instances, the triggered assessments according to a predetermined time schedule are regular stain quality assessments.

The spectra processing circuitry is specifically configured or programmed to perform the functions according to the methods as described herein, including spectral measurements functions and analysis tasks, and may include at least one data processing unit for performing data related functions.

By "data processing unit", as used herein, is meant any hardware and/or software combination that will perform the functions required of it. For example, any data processing unit herein may be a programmable digital microprocessor such as available in the form of an electronic controller, mainframe, server or personal computer (desktop or portable). Where the data processing unit is programmable, suitable programming can be communicated from a remote location to the data processing unit, or previously saved in a computer program product (such as a portable or fixed computer readable storage medium, whether magnetic, optical or solid state device based).

Substantially any circuitry can be configured to a functional arrangement within the devices and systems for performing the methods disclosed herein. The hardware architecture of such circuitry, including e.g., a specifically configured computer, is well known by a person skilled in the art, and can comprise hardware components including one or more processors (CPU), a random-access memory (RAM), a read-only memory (ROM), an internal or external data storage medium (e.g., hard disk drive). Such circuitry can also comprise one or more graphic boards for processing and outputting graphical information to display means. The above components can be suitably interconnected via a bus within the circuitry, e.g., inside a specific-use computer. The circuitry can further comprise suitable interfaces for communicating with general-purpose external components such as a monitor, keyboard, mouse, network, etc. In some embodiments, the circuitry can be capable of parallel processing or can be part of a network configured for parallel or distributive computing to increase the processing power for the present methods and programs. In some embodiments, the program code read out from the storage medium can be written into a memory provided in an expanded board inserted in the circuitry, or an expanded unit connected to the circuitry, and a CPU or the like provided in the expanded board or expanded unit can actually perform a part or all of the operations according to the instructions of the programming, so as to accomplish the functions described.

The devices and systems of the instant disclosure may further include a "memory" that is capable of storing information such that it is accessible and retrievable at a later date by a computer. Any convenient data storage structure may be chosen, based on the means used to access the stored information. In certain aspects, the information may be stored in a "permanent memory" (i.e. memory that is not erased by termination of the electrical supply to a computer or processor) or "non-permanent memory". Computer hard-drive, CD-ROM, floppy disk, portable flash drive and DVD are all examples of permanent memory. Random Access Memory (RAM) is an example of non-permanent memory. A file in permanent memory may be editable and re-writable.

In addition to the components of the devices and systems of the instant disclosure, e.g., as described above, systems of the disclosure may include a number of additional components, such as data output devices, e.g., monitors and/or speakers, data input devices, e.g., interface ports, keyboards, etc., fluid handling components, power sources, etc.

Computer Readable Media

The instant disclosure includes computer readable medium, including non-transitory computer readable medium, which stores instructions for spectrophotometric methods for assessing histological stains used in a histology analyzer. Aspects of the instant disclosure include computer readable medium storing instructions that, when executed by a computing device, cause the computing device to measure spectrophotometric characteristics of a subject histological stain using a spectrophotometer to identify one or more characteristics that are specific to a particular stain and/or stain formulation and make an assessment of the stain or formulation.

In some instances, a computer readable medium of the instant disclosure stores instructions that cause a computing device to perform one or more of the steps of assessing a subject histological stain according to the methods as described herein. For example, in some instances, a computer readable medium of the instant disclosure stores instructions that cause a computing device to make a comparison of measured spectral characteristics and spectral characteristics stored in a library. In some instances, a computer readable medium of the instant disclosure stores instructions that cause a computing device to make a determination, e.g., of stain identity or stain quality, based on the comparison of measured spectral characteristics and spectral characteristics stored in a library.

In some instances, a computer readable medium of the instant disclosure stores a library of reference spectral characteristics, e.g., as described herein, of various histological stains and/or various formulations of histological stains for use in performing the methods as described herein. Such a computer readable medium may or may not be a component of a larger device or system, e.g., as described herein. Such a computer readable medium may or may not be removable from a larger device or system, e.g., as described herein. In some instances, the library may be specific for a particular category of histological stains, e.g., a computer readable medium may store a library of reference spectral characteristics specifically for Romanowsky stains, including for e.g., any or all of the reference spectral characteristics described herein for Romanowsky stains. In some instances, the a computer readable medium of the instant disclosure stores a library of reference spectral characteristics that includes but is not limited to e.g., reference spectral characteristics for May Grunwald, Wright Giemsa or May Grunwals Giemsa or a combination thereof.

In some instances, a computer readable medium of the instant disclosure stores at least both instructions that cause a computing device to perform one or more of the steps of assessing a subject histological stain according to the methods as described herein and a library of reference spectral characteristics. In some instances, a computer readable medium storing both instructions that cause a computing device to perform one or more of the steps of assessing a subject histological stain according to the methods as described herein and a library of reference spectral characteristics is specific for Romanowsky stains and includes reference spectral characteristics for May Grunwald, Wright Giemsa or May Grunwals Giemsa or a combination thereof.

In certain embodiments, instructions in accordance with the methods described herein can be coded onto a computer-readable medium in the form of "programming", where the term "computer readable medium" as used herein refers to any storage or transmission medium that participates in providing instructions and/or data to a computer for execution and/or processing. Examples of storage media include a floppy disk, hard disk, optical disk, magneto-optical disk, CD-ROM, CD-R, magnetic tape, non-volatile memory card, ROM, DVD-ROM, Blue-ray disk, solid state disk, and network attached storage (NAS), whether or not such devices are internal or external to the computer. A file containing information can be "stored" on computer readable medium, where "storing" means recording information such that it is accessible and retrievable at a later date by a computer.

The computer-implemented method described herein can be executed using programming that can be written in one or more of any number of computer programming languages. Such languages include, for example, Java (Sun Microsystems, Inc., Santa Clara, Calif.), Visual Basic (Microsoft Corp., Redmond, Wash.), and C++ (AT&T Corp., Bedminster, N.J.), as well as any many others.

The following examples are offered by way of illustration and not by way of limitation.

EXAMPLES

Example 1

Stain Sample Preparation

Romanowsky stains, including Wright Giemsa (WG) and May Grunwald (MG) stains, were prepared to include stain compositions that were within specifications and intentionally outside of specification. Specifically, stains were prepared that were below specification, within specification but below target, at target, within specification but above target and above specification. Peak absorbance measurements at about 655 nm for the prepared target and off-target stains as 1:200 dilutions in deionized water (DI) are provided in Table 1 (FIG. 1).

Example 2

Determination of Absorbance Lower Limits

The initial absorbance of the differently prepared WG and MG stains were determined at 655 nm and 517 nm and are provided in Tables 2 and 3, respectively.

TABLE 2

| WG Sample | 655 nm | 517 nm |
|---|---|---|
| 50% low spec | 0.481 | 0.330 |
| 67% low spec | 0.656 | 0.490 |
| 83% low spec | 0.798 | 0.620 |
| 100% low spec | 0.951* | 0.765* |
| target | 1.052 | 0.880 |
| 100% high spec | 1.128 | 0.978 |
| 110% high spec | 1.249 | 1.104 |

TABLE 3

| MG Sample | 655 nm | 517 nm |
|---|---|---|
| 50% low spec | 0.298 | 0.257 |
| 67% low spec | 0.398 | 0.362 |
| 83% low spec | 0.499 | 0.481 |
| 100% low spec | 0.600 | 0.597 |
| target | 0.682 | 0.713 |
| 100% high spec | 0.779 | 0.840 |
| 110% high spec | 0.888 | 0.997 |

Absorbance measurements of the stains were performed according to the following procedure using 1:200 dilutions of each stain in DI water:

1. Using a pipettor, a 250 μL aliquot of the stain sample was placed in a 50 mL volumetric flask.
2. The volumetric flask was filled to the 50 mL mark using DI water to arrive at a 1:200 stain dilution.
3. The volumetric flask was capped and mixed by inverting the flask 3-4 times.
4. Steps 1-3 were repeated two more times, to generate a total of 3 independent diluted sample replicates for each stain sample.
5. OD scans (200-800 nm) were performed on all prepared 1:200 dilutions according to the following procedure:
5.1. The absorbance baseline was recorded on the instrument using a cuvette (quartz) filled with 3 mL of DI water (solvent).
5.2. An OD scan was run on the stain aliquot and max absorbance was recorded for the 2 highest peaks (typically ~650 nm and ~525 nm).
5.3. Steps 5.1 and 5.2 were repeated for the 2 additional independent diluted sample replicates.
5.4. The absorbance files from the spectrophotometer were stored in a computer file.

Figure 2:
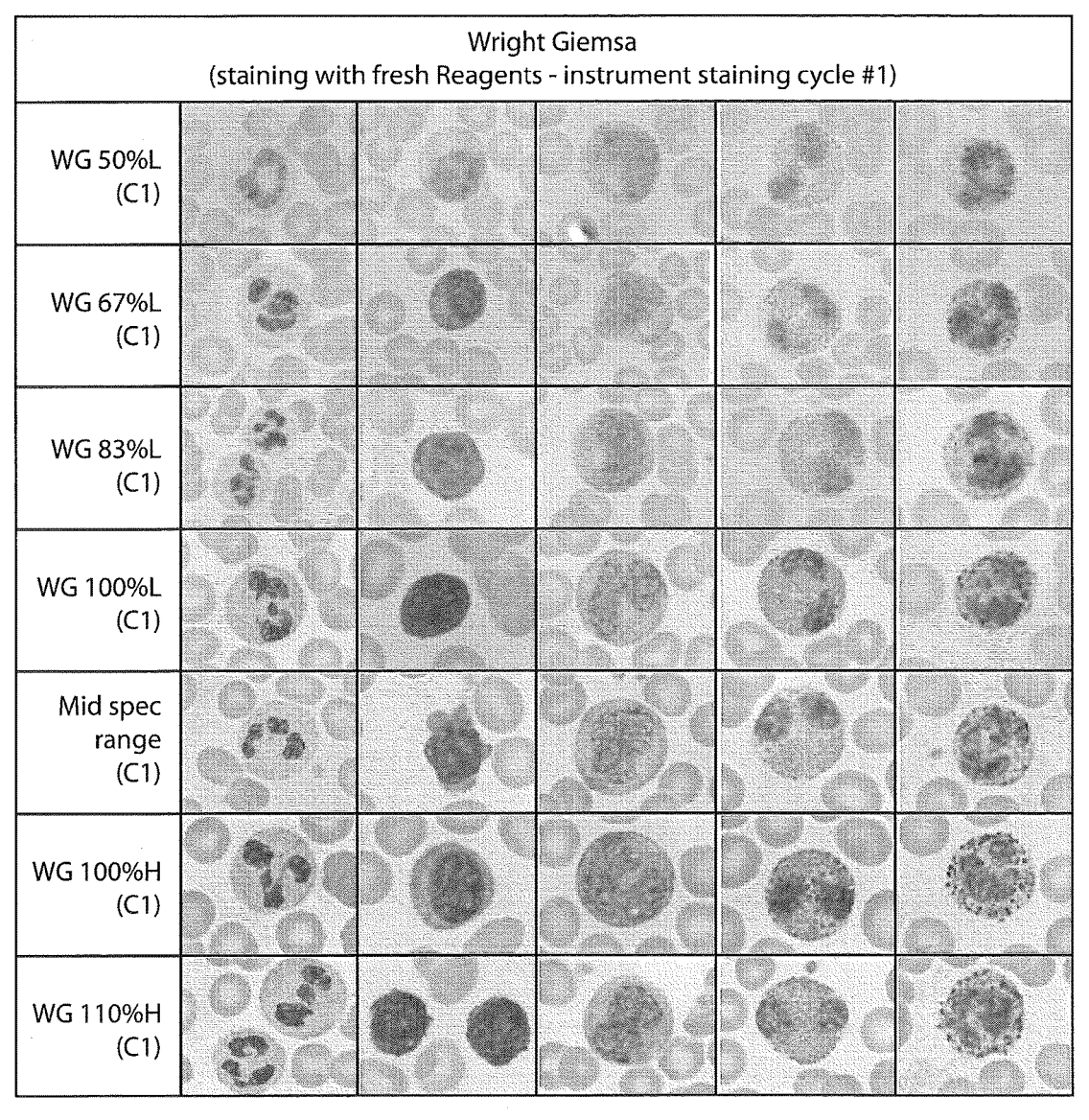

For comparison of cell coloration between the different WG stain samples with different absorbance values and different dye concentrations example images are provided (FIG. 2). For comparison of cell coloration between the different MG stain samples with different absorbance values and different dye concentrations example images are also provided (FIG. 3).

Example 3

Spectral Discrimination of Different Romanowsky Stains

Wright Giemsa and May Grunwald stains were discriminated using spectral absorption measurements. Absorption spectrum was measured for a stain in the spectral region of 200-800 nm with a 1.0 nm step. An exact position of the peak in the spectral range of 650-665 nm was identified with an accuracy of ±1.0 nm. For the particular stain formulations and absorbance measurements used in this example, when the absorption peak position was located at $\lambda=659$ nm±1 nm, the stain was recognized as Wright Giemsa, whereas when the peak position was located at $\lambda=655$ nm±1 nm, the stain was identified as May Grunwald (see FIG. 4A-4B).

To increase precision of the measurements and reliability of the conclusion, measurement of absorption spectra can be repeated for several concentrations of the original specimens to monitor spectral positions of the peaks as absorption values either increase or decrease. As observed, the peak identification wavelengths remain constant (see FIG. 5A-5B and FIG. 6A-6B).

Both WG and MG stains are mixtures of similar initial compounds, which nonetheless have small but measurable differences in the absorption spectra due to slightly different formulations of those compounds. Wright Giemsa stain is classically a mixture of azure, eosin and methylene blue dyes while May Grunwald is composed of eosin and methylene blue dyes. Different types of azure have absorption peaks which vary in the range of $\lambda\sim647-659$ nm while eosin absorption peaks are located in the region $\lambda\sim515-530$ nm. A useful Wright Giemsa formulation used in hematology and automated hematology instruments has two absorption peaks located respectively at 517 nm±1 nm and 659 nm±1 nm whereas a useful May Grunwald formulation used in hematology and automated hematology instruments has peaks positioned at 517 nm±1 nm and 655 nm±1 nm. Therefore, the spectral shift of $\Delta\lambda=3$ nm of the red peak provides a means to discriminate these two types of stains.

Figure 4A:
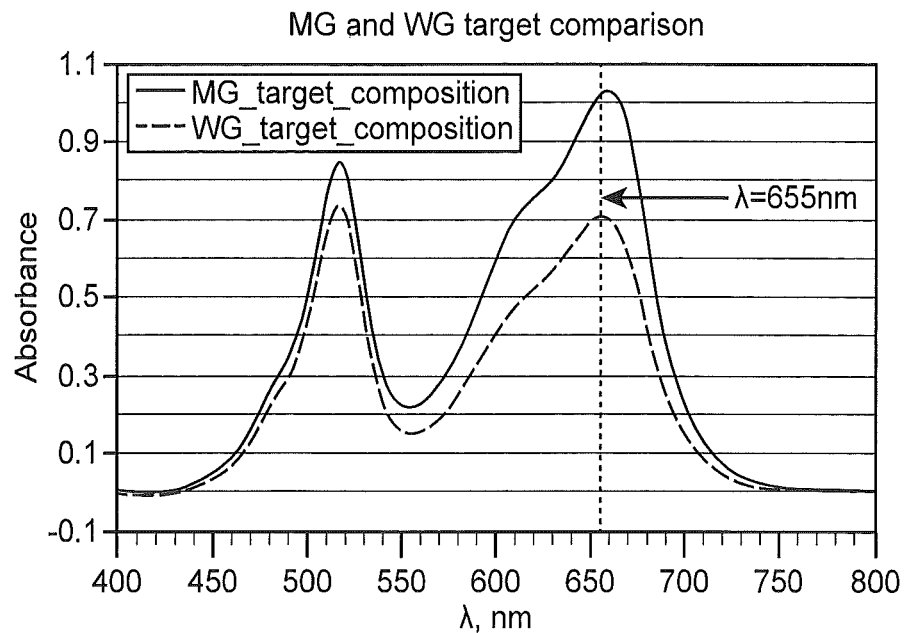
FIGS. 4A and 4B depicts absorption spectra of WG and MG stains having various formulations and concentrations.
Figure 4B:
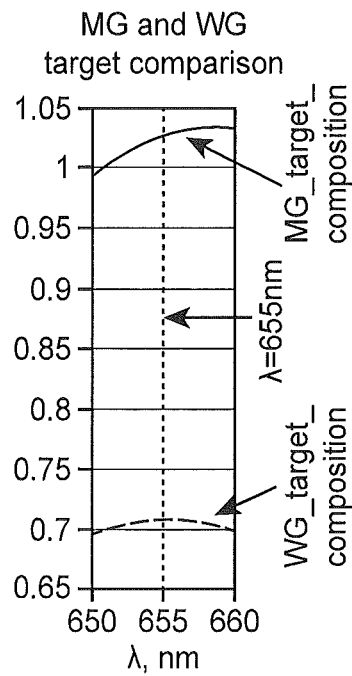

FIG. 4A-4B: Absorption spectra of Wright Giemsa and May Grunwald stains having targeted formulations and concentrations (FIG. 4A) showing a distinct spectral shift of the red peak by $\Delta\lambda=3$ nm between the two stains (FIG. 4B). Absorption spectra of these stains prepared at various concentrations of their targeted formulations demonstrate decreased absorbance values of the peaks while the spectral shift of the red peak $\Delta\lambda=3$ nm remains constant.

Figure 5A:
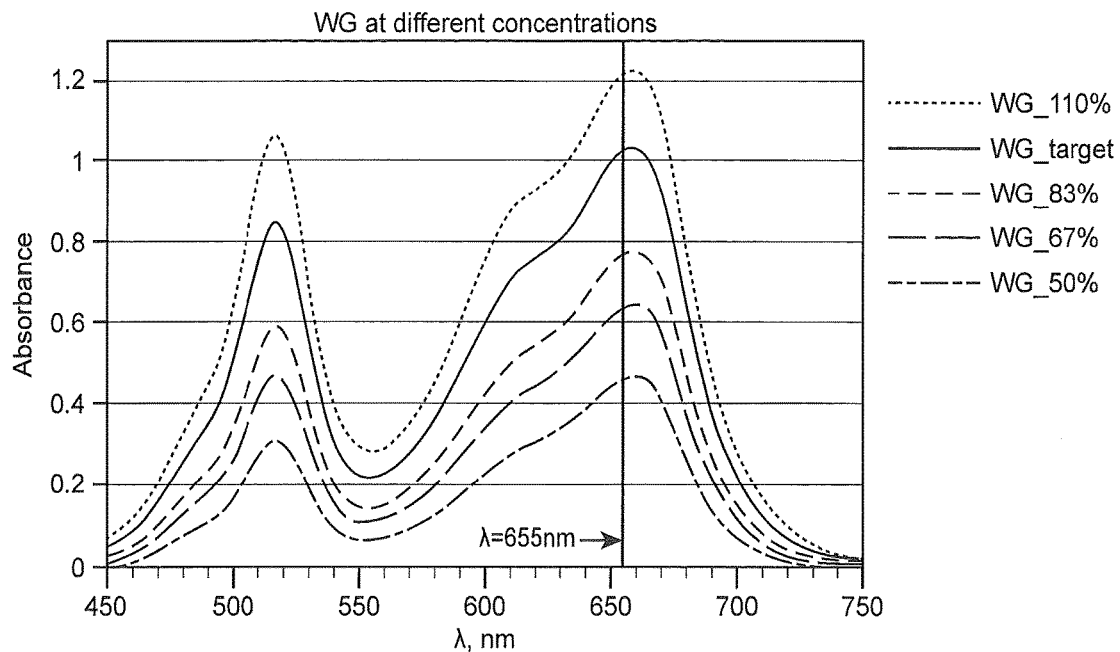
FIGS. 5A and 5B depicts absorption spectra of WG and MG stains prepared at different concentrations of their targeted formulations.
Figure 5B:
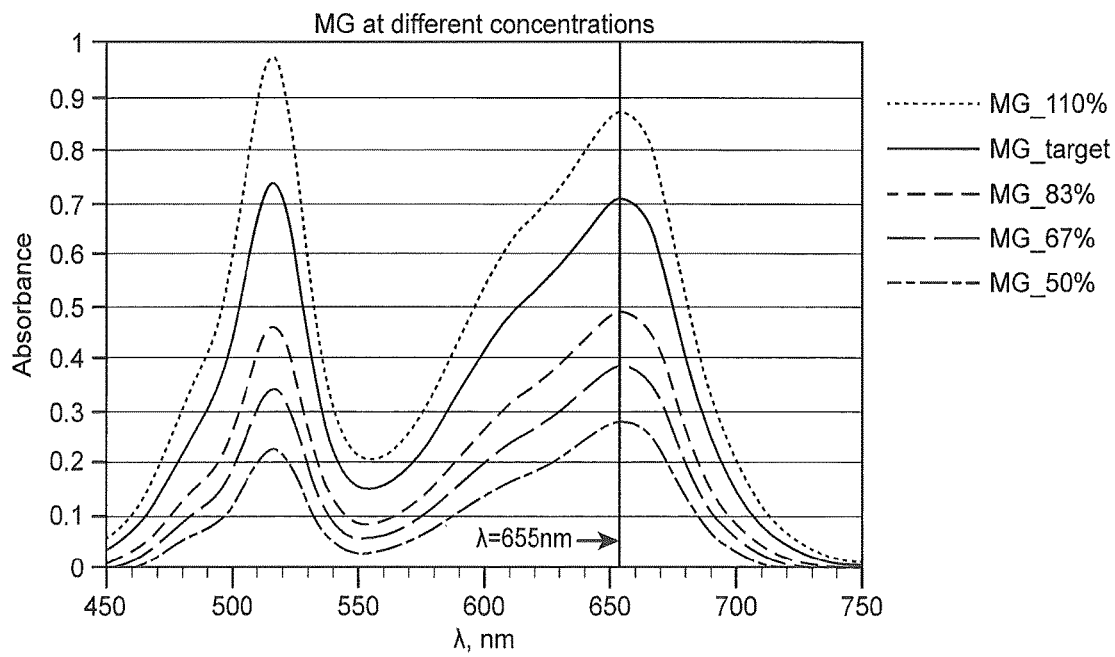

FIG. 5A-5B: Absorption spectra of Wright Giemsa (FIG. 5A) and May Grunwald (FIG. 5B) stains prepared at different concentrations of their targeted formulations demonstrate that the positions of the absorption peaks in the read area are unique to each type of stain and are concentration independent.

Figure 6B:
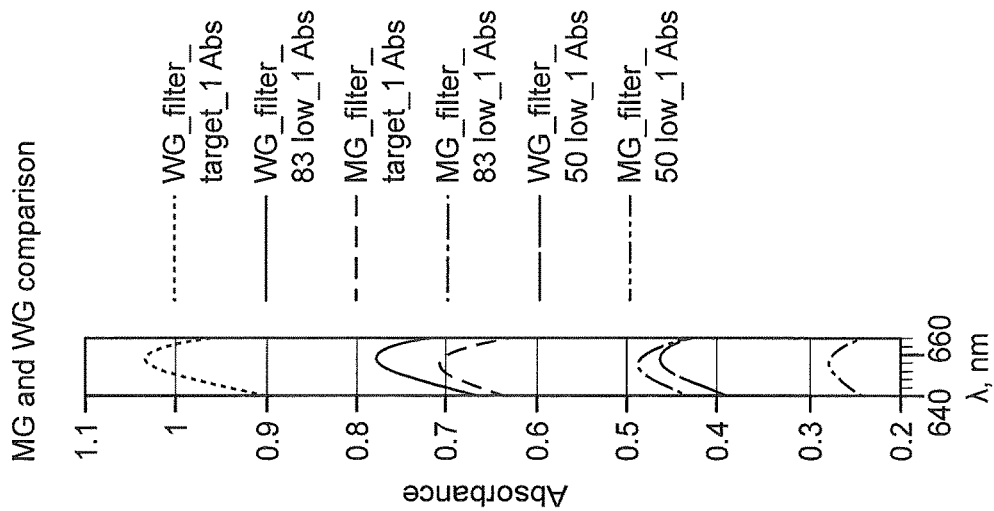
FIGS. 6A and 6B depicts a comparison between absorption spectra of WG and MG stains prepared at different concentrations of their targeted formulations.
Figure 6A:
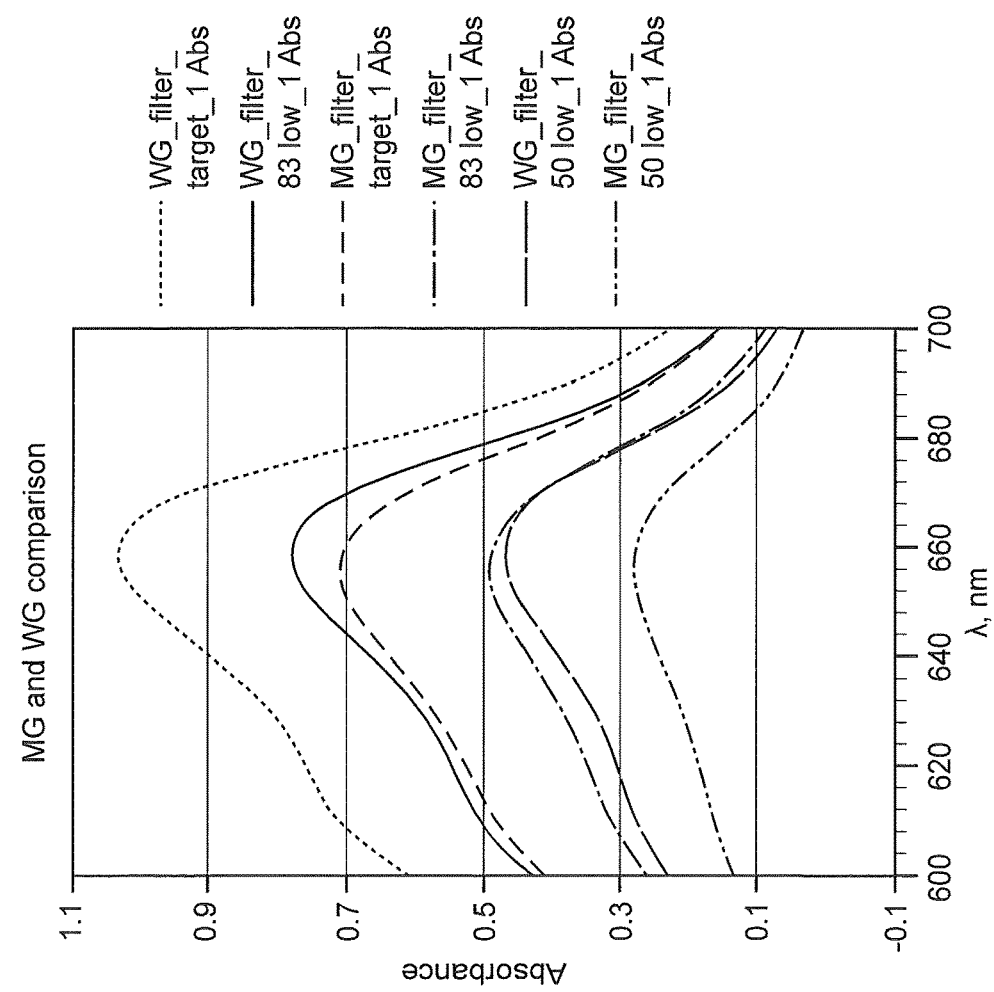

FIG. 6A-6B: Comparison between absorption spectra of Wright Giemsa and May Grunwald stains prepared at different concentrations of their targeted formulations (FIG. 6A-6B). Absorption spectra of these stains demonstrate various absorbance values of the peaks while a spectral shift of the red peak $\Delta\lambda = 3$ nm remains constant across various stain concentrations (FIG. 6B).

Figure 7B:
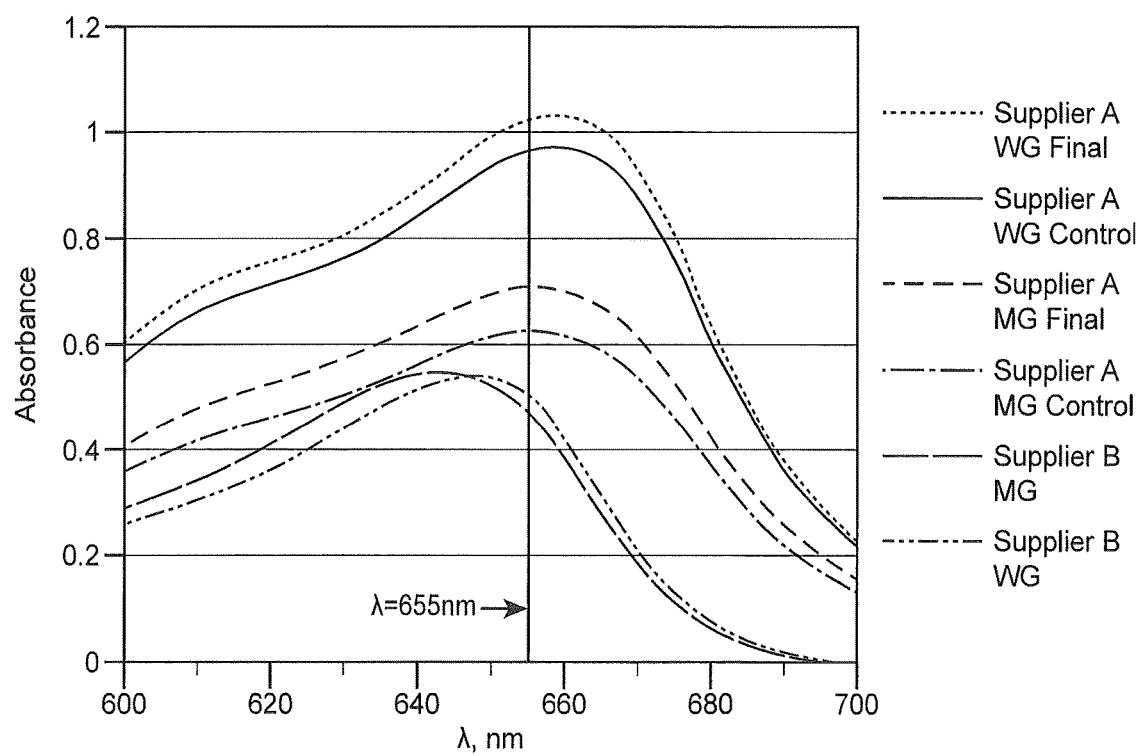

Absorption spectra of Wright Giemsa and May Grunwald stains from different manufacturers (i.e. suppliers) are prepared in slightly different formulations. These differing formulations have distinct spectral positions of absorbance peaks. For example, as demonstrated in FIGS. 7A and 7B the spectral positions of absorbance peaks in the red spectral region can be used to differentiate stains from two different manufacturers (i.e., "Supplier A" and "Supplier B"). the spectral shift of the red peak ($\Delta\lambda$) between the peaks of the stains from the different suppliers can be used to positively identify the specific stain ($\lambda = 655$ nm$\pm\Delta\lambda$).

Figure 8:
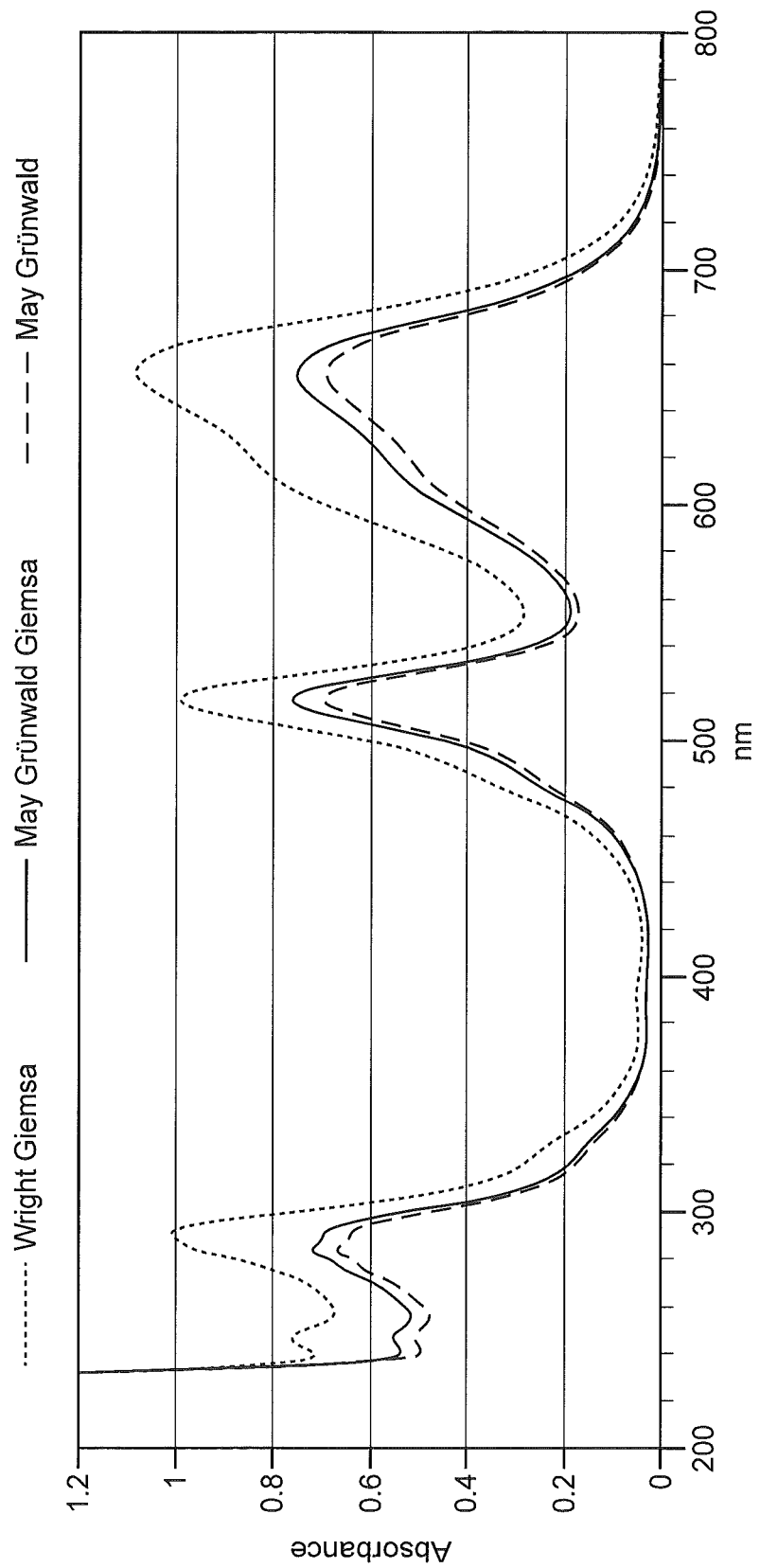
FIG. 8 depicts the different spectra across 200 nm to 800 nm for MG, May Grunwald Giemsa (MGG) and WG, demonstrating unique spectral characteristics between the three stains.

FIG. 8: extended spectra covering 200 nm to 800 nm further demonstrate the unique absorbance profiles of individual stains. Unique peaks in the UV range may be used to discriminate one stain from another.

Absorbance spectra for MG, MGG and WG in the spectral region 200 nm to 800 nm (FIG. 8) demonstrates the three main absorption bands, positioned at ~293 nm (Methylene blue), ~520 nm (Eosin), ~664 nm (Methylene blue) and shoulder at ~610 nm (Methylene blue) characteristic of the stain formulations. Spectral shifts of the peak positions with respect to the main absorbance bands of pure dyes, as well as broadness of the peaks and their corresponding ratios are unique characteristics of the specific stain formulations.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A method of assessing a histological stain used in a histology analyzer, the method comprising:
   a) measuring on a spectrophotometer the absorbance spectrum of the histological stain over a predefined range;
   b) identifying:
      one or more wavelengths of peak absorbance from the measured spectrum, and
      a peak-width-at-half-maximum absorbance value from the measured spectrum;
   c) comparing the one or more identified wavelengths of peak absorbance to a library;
   d) comparing the identified peak-width-at-half-maximum-absorbance value to the library; wherein the library comprises:
      reference wavelengths of peak absorbance for a plurality of histological stains, and
      a plurality of peak-width-at-half-maximum-absorbance values for a plurality of histological stains; and
   (e) assessing the histological stain based on the comparison.

2. The method of claim 1, wherein the assessing comprises determining the identity of the histological stain.

3. The method of claim 1, wherein the assessing comprises determining the quality of the histological stain.

4. The method of claim 1, wherein the method further comprises generating a report of the assessment.

5. The method of claim 4, wherein the report comprises stain-specific information selected from the group consisting of: the identity of the histological stain, the quality of the histological stain, one or more wavelengths of peak absorbance, one or more absorbance measurements over the predefined range or a portion thereof, and combinations thereof.

6. The method of claim 1, wherein the predefined range is or is within 200 nm to 800 nm.

7. The method of claim 1, wherein the predefined range is or is within 500 nm to 700 nm.

8. The method of claim 1, wherein the predefined range is or is within 600 nm to 700 nm.

9. The method of claim 1, wherein the predefined range is or is within 640 nm to 670 nm.

10. The method of claim 1, wherein the predefined range is or is within 500 nm to 550 nm.

11. The method of claim 6, wherein the predefined range is or is within 200 nm to 400 nm.

12. The method of claim 1, wherein method comprises measuring on a spectrophotometer the absorbance spectrum of the histological stain over two or more predefined ranges.

13. The method of claim 12, wherein the two or more predefined ranges comprise a first predefined range that is or is within 500 nm to 700 nm and a second predefined range that is or is within 200 nm to 400 nm.

14. The method of claim 1, wherein the method further comprises diluting the histological stain prior to measuring the absorbance spectrum with a solvent and the dilution and the solvent specifically correspond to the reference wavelengths of peak absorbance for the plurality of histological stains.

15. The method of claim 14, wherein the diluting comprises diluting 1:200 with water.

16. The method of claim 1, wherein the method further comprises preparing a plurality of dilutions of the histological stain and performing steps (a) through (d) for each dilution of the plurality of dilutions of the histological stain.

17. The method of claim 16, wherein the method comprises preparing a first dilution and a second dilution, wherein the second dilution is half the concentration of the first dilution.

18. The method of claim 1, wherein the identifying further comprises identifying a spectral shift value from the measured spectrum, the library further comprises a plurality of spectral shift values for a plurality of histological stains and the comparing further comprises comparing the spectral shift value to the library.

19. The method of claim 1, wherein the plurality of histological stains comprises Romanowsky stains.

20. The method of claim 19, wherein the Romanowsky stains are selected from the group consisting of Wright Giemsa, May Grunwald and May Grunwals Giemsa.

21. The method of claim 1, wherein the absorbance spectrum is measured with a resolution of at least 1 nm.

22. The method of claim 1, wherein the library comprises a reference wavelength peak of absorbance at 656 nm for May Grunwald.

23. The method of claim 1, wherein the library comprises a plurality of spectral shift values for a plurality of May Grunwald stain compositions wherein the spectral shift value is measured from the reference wavelength peak of absorbance of 656 nm for May Grunwald.

24. The method of claim 1 wherein the library comprises a plurality of peak-width-at-half-maximum-absorbance values for a plurality of May Grunwald stain compositions.

25. The method of claim 1, wherein the library comprises a reference wavelength peak of absorbance at 659 nm for Wright Giemsa.

26. The method of claim 1, wherein the library comprises a plurality of spectral shift values for a plurality of Wright Giemsa stain compositions wherein the spectral shift value is measured from the reference wavelength peak of absorbance of 659 nm for Wright Giemsa.

27. The method of claim 1, wherein the library comprises a plurality of peak-width-at-half-maximum-absorbance values for a plurality of Wright Giemsa stain compositions.

28. The method of claim 1, wherein the library comprises a reference wavelength peak of absorbance for May Grunwald Giemsa.

29. The method of claim 1, wherein the library comprises a plurality of spectral shift values for a plurality of May Grunwald Giemsa stain compositions wherein the spectral shift value is measured from a reference wavelength peak of absorbance for May Grunwald Giemsa.

30. The method of claim 1, wherein the library comprises a plurality of peak-width-at-half-maximum-absorbance values for a plurality of May Grunwald Giemsa stain compositions.

31. The method of claim 1, wherein the method comprises making a plurality of assessments of the histological stain over time in order to monitor stain quality.

32. The method of claim 1, wherein the method comprises transferring an aliquot of the histological stain from a storage container into an analysis vessel prior to the measuring.

33. The method of claim 32, wherein the analysis vessel is selected from the group consisting of a cuvette, a capillary and a multi-well plate.

34. The method of claim 1, wherein the measuring takes place within the histology analyzer.

35. The method of claim 1, wherein the measuring takes place outside the histology analyzer.

36. The method according to claim 35, wherein after the measuring is performed outside the histology analyzer the absorbance spectrum of the histological stain, one or more wavelengths of peak absorbance derived therefrom or a combination thereof is transferred to the histology analyzer.

37. The method according to claim 36, wherein the absorbance spectrum of the histological stain, one or more wavelengths of peak absorbance derived therefrom or a combination thereof is transferred through a wired data connection connecting the spectrophotometer to the histology analyzer.

38. The method according to claim 36, wherein the absorbance spectrum of the histological stain, one or more wavelengths of peak absorbance derived therefrom or a combination thereof is transferred using a computer-readable storage medium.

* * * * *